US009249105B2

(12) United States Patent
Fatheree et al.

(10) Patent No.: US 9,249,105 B2
(45) Date of Patent: *Feb. 2, 2016

(54) CRYSTALLINE FORMS OF AN ALKOXYIMIDAZOL-1-YLMETHYL BIPHENYL CARBOXYLIC ACID

(71) Applicants: Paul R. Fatheree, San Francisco, CA (US); Venkat R. Thalladi, Foster City, CA (US)

(72) Inventors: Paul R. Fatheree, San Francisco, CA (US); Venkat R. Thalladi, Foster City, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/317,060

(22) Filed: Jun. 27, 2014

(65) Prior Publication Data

US 2015/0133518 A1 May 14, 2015

Related U.S. Application Data

(63) Continuation of application No. 13/720,395, filed on Dec. 19, 2012, now Pat. No. 8,802,709, which is a continuation of application No. 13/292,370, filed on Nov. 9, 2011, now Pat. No. 8,362,060.

(60) Provisional application No. 61/412,011, filed on Nov. 10, 2010.

(51) Int. Cl.
*A61K 31/4166* (2006.01)
*C07D 233/66* (2006.01)
*C07D 233/70* (2006.01)
*A61K 31/4164* (2006.01)
*A61K 45/06* (2006.01)

(52) U.S. Cl.
CPC .......... *C07D 233/70* (2013.01); *A61K 31/4164* (2013.01); *A61K 45/06* (2013.01); *C07B 2200/13* (2013.01)

(58) Field of Classification Search
CPC .................... A61K 31/4166; C07D 233/66
USPC ........................ 548/316.4; 514/398
See application file for complete search history.

(56) References Cited

U.S. PATENT DOCUMENTS

| | | | |
|---|---|---|---|
| 7,855,221 B2 * | 12/2010 | Chao | C07D 233/70 514/398 |
| 7,879,896 B2 | 2/2011 | Allegretti et al. | |
| 8,013,005 B2 | 9/2011 | Allegretti et al. | |
| 2011/0077411 A1 | 3/2011 | Zhang et al. | |

FOREIGN PATENT DOCUMENTS

WO  2011109579 A1  9/2011

OTHER PUBLICATIONS

Brittain, "Polymorphism in Pharmaceutical Solids", Drugs and the Pharmaceutical Sciences, vol. 192, 2nd edition, pp. 1-3, 79-80, 87-92, 94, 318, 334-335, and 611-612.
International Search Report for PCT/US2011/109579 dated Feb. 3, 2012.
Berge et al., J. Pharm. Sciences, vol. 66(1), 1977, pp. 1-18.
Gould, International J. of Therapeutics, vol. 33, 1986, pp. 201-213, 217.
Kawaguchi et al. "Drug and Crystal Polymorphism", Journal of Human Environmental Engineering, 2002, 4(2), 310-317. [In Japanese].
Morissette et al., Advanced Drug Delivery Reviews, 2004, 56, 275-300.
Ooshima, "Crystallization of Polymorphs and Pseudo-polymorphs and Its Control", Pharm Stage, 2007, 6(10), 48-53. [In Japanese].
ICH-Q6A: Test Procedures and Acceptance Criteria for New Drug Substances and New Drug Products. Chemical Substances, Pharmaceutical Affairs Bureau, Notification #568, May 1, 2001. [In Japanese].
Takata, "API Form Screening and Selection in Drug Discovery Stage", Pharm Stage, 2007, 6(10), 20-25. [In Japanese].
Yamano, "Approach to Crystal Polymorph in Process Research of New Drug", Journal of Synthetic Organic Chemistry, Japan, 2007, 65(9), 907-913. [In Japanese].

* cited by examiner

*Primary Examiner* — Kamal Saeed
*Assistant Examiner* — Janet L Coppins
(74) *Attorney, Agent, or Firm* — Jeffrey A. Hagenah

(57) ABSTRACT

The invention provides crystalline salt forms of 4'-{2-ethoxy-4-ethyl-5-[((S)-2-mercapto-4-methylpentanoylamino)methyl]-imidazol-1-ylmethyl}-3'-fluorobiphenyl-2-carboxylic acid. This invention also provides pharmaceutical compositions comprising the crystalline compounds, processes and intermediates for preparing the crystalline compounds, and methods of using the crystalline compounds to treat diseases such as hypertension.

7 Claims, 11 Drawing Sheets

CRYSTALLINE FORMS OF AN ALKOXYIMIDAZOL-1-YLMETHYL BIPHENYL CARBOXYLIC ACID

CROSS-REFERENCE TO RELATED APPLICATIONS

This application is a continuation of U.S. Ser. No. 13/720, 395, now allowed; which is a continuation of U.S. Ser. No. 13/292,370, now U.S. Pat. No. 8,362,060; which claims the benefit of U.S. Provisional Application No. 61/412,011, filed on Nov. 10, 2010; the entire disclosures of which are incorporated herein by reference.

BACKGROUND OF THE INVENTION

1. Field of the Invention

The present invention relates to novel crystalline forms of an alkoxyimidazol-1-ylmethyl biphenyl carboxylic acid, which has angiotensin II type 1 receptor antagonist activity and neprilysin-inhibition activity. This invention also relates to pharmaceutical compositions comprising the crystalline compounds or prepared from such compounds, processes and intermediates for preparing the crystalline compounds and methods of using such compounds to treat diseases such as hypertension.

2. State of the Art

Commonly-assigned U.S. Publication Nos. 2008/0269305 and 2009/0023228, both to Allegretti et al. filed on Apr. 23, 2008, disclose novel compounds that possess $AT_1$ receptor antagonist activity and neprilysin (NEP) enzyme inhibition activity, the disclosures of which are incorporated herein by reference. In particular, the compound, 4'-{2-ethoxy-4-ethyl-5-[((S)-2-mercapto-4-methylpentanoylamino)methyl]imidazol-1-ylmethyl}-3'-fluorobiphenyl-2-carboxylic acid is specifically disclosed in these applications.

The chemical structure of 4'-{2-ethoxy-4-ethyl-5-[((S)-2-mercapto-4-methylpentanoylamino)methyl]imidazol-1-ylmethyl}-3'-fluorobiphenyl-2-carboxylic acid is represented by formula I:

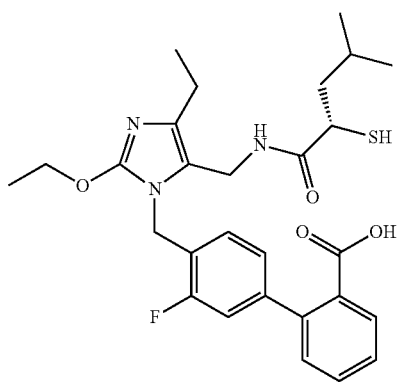

(I)

When preparing compounds for long term storage and when preparing pharmaceutical compositions and formulations, it is often desirable to have a crystalline form of the therapeutic agent that is neither hygroscopic nor deliquescent. It is also advantageous to have a crystalline form that has a relatively high melting point (i.e., greater than about 100° C.), which allows the material to be processed, for example, micronized, without significant decomposition.

Although a crystalline freebase form of the compound of formula I has been reported in U.S. Patent Publication No. 2010/0081697 by Chao et al., the crystalline forms of the present invention have different and particularly useful properties, including better solubility and improved stability.

SUMMARY OF THE INVENTION

One aspect of the invention relates to a crystalline hemiedisylate salt of 4'-{2-ethoxy-4-ethyl-5-[((S)-2-mercapto-4-methylpentanoylamino)methyl]imidazol-1-ylmethyl}-3'-fluorobiphenyl-2-carboxylic acid, designated as form I, characterized by a powder x-ray diffraction pattern comprising diffraction peaks at 2θ values of 9.89±0.20, 11.66±0.20, 13.55±0.20, 18.41±0.20, 20.42±0.20, and 22.46±0.20.

Another aspect of the invention relates to a crystalline hemiedisylate salt of 4'-{2-ethoxy-4-ethyl-5-[((S)-2-mercapto-4-methylpentanoylamino)methyl]imidazol-1-ylmethyl}-3'-fluorobiphenyl-2-carboxylic acid, designated as form II, characterized by a powder x-ray diffraction pattern comprising diffraction peaks at 2θ values of 9.74±0.20, 11.00±0.20, 12.89±0.20, 14.27±0.20, 15.54±0.20, 18.62±0.20, and 23.78±0.20.

Still another aspect of the invention relates to a crystalline heminapadisylate salt of 4'-{2-ethoxy-4-ethyl-5-[((S)-2-mercapto-4-methylpentanoylamino)methyl]imidazol-1-ylmethyl}-3'-fluorobiphenyl-2-carboxylic acid, characterized by a powder x-ray diffraction pattern comprising diffraction peaks at 2θ values of 4.84±0.20, 9.41±0.20, 10.82±0.20, 17.39±0.20, 24.17±0.20, and 24.65±0.20.

Yet another aspect of the invention relates to a crystalline mono-oxalate salt of 4'-{2-ethoxy-4-ethyl-5[((S)-2-mercapto-4-methylpentanoylamino)methyl]imidazol-1-ylmethyl}-3'-fluorobiphenyl-2-carboxylic acid, characterized by a powder x-ray diffraction pattern comprising diffraction peaks at 2θ values of 6.1±0.20, 11.0±0.20, 13.0±0.20, 14.4±0.20, 15.2±0.20, 16.5±0.20, 17.3±0.20, 18.4±0.20, 21.9±0.20, 23.9±0.20, 24.3±0.20, 24.5±0.20, and 26.1±0.20.

Another aspect of the invention relates to processes for preparing crystalline forms of the compound of formula I. In one embodiment, a process for preparing a crystalline form of 4'-{2-ethoxy-4-ethyl-5-[((S)-2-mercapto-4-methylpentanoylamino)-methyl]imidazol-1-ylmethyl}-3'-fluorobiphenyl-2-carboxylic acid comprises a) treating 4'-{2-ethoxy-4-ethyl-5-[((S)-2-mercapto-4-methylpentanoylamino)methyl]imidazol-1-ylmethyl}-3'-fluorobiphenyl-2-carboxylic acid with an appropriate counterion; b) optionally heating, stirring or sonicating to complete dissolution; and c) allowing solids to form and isolating the solids to yield the crystalline form.

Another aspect of the invention relates to a process for purifying 4'-{2-ethoxy-4-ethyl-5-[((S)-2-mercapto-4-methylpentanoylamino)methyl]imidazol-1-ylmethyl}-3'-fluorobiphenyl-2-carboxylic acid. In one embodiment, this process comprises forming a crystalline form of 4'-{2-ethoxy-4-ethyl-5-[((S)-2-mercapto-4-methylpentanoylamino)-methyl]imidazol-1-ylmethyl}-3'-fluorobiphenyl-2-carboxylic acid. The invention also relates to products prepared by the processes described herein. In specific embodiments, the crystalline form is a hemiedisylate salt form I, hemiedisylate salt form II, heminapadisylate salt, or mono-oxalate salt.

One aspect of the invention relates to a pharmaceutical composition comprising a pharmaceutically acceptable carrier and a crystalline form of 4'-{2-ethoxy-4-ethyl-5-[((S)-2-mercapto-4-methylpentanoylamino)methyl]imidazol-1-ylmethyl}-3'-fluorobiphenyl-2-carboxylic acid. In specific embodiments, the crystalline form is a hemiedisylate salt form I, hemiedisylate salt form II, heminapadisylate salt, or mono-oxalate salt.

Another aspect of the invention relates to compositions comprising a crystalline form of the compound of formula I in combination with one or more other therapeutic agents. Accordingly, in one embodiment, the invention relates to a composition comprising (a) a pharmaceutically acceptable carrier and a therapeutically effective amount of a crystalline form of the compound of formula I; and (b) a therapeutically effective amount of an agent selected from diuretics, $\beta_1$ adrenergic receptor blockers, calcium channel blockers, angiotensin-converting enzyme inhibitors, $AT_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, vasopressin receptor antagonists, and combinations thereof; wherein the crystalline form and the agent are formulated together or separately. When the agent is formulated separately, a pharmaceutically acceptable carrier may be included. In specific embodiments, the crystalline form is a hemiedisylate salt form I, hemiedisylate salt form II, heminapadisylate salt, or mono-oxalate salt.

Yet another aspect of the invention relates to a method for treating hypertension or heart failure, comprising administering to a patient in need of treatment a therapeutically effective amount of a crystalline form of 4'-{2-ethoxy-4-ethyl-5-[((S)-2-mercapto-4-methylpentanoylamino)methyl]imidazol-1-ylmethyl}-3'-fluorobiphenyl-2-carboxylic acid. In specific embodiments, the crystalline form is a hemiedisylate salt form I, hemiedisylate salt form II, heminapadisylate salt, or mono-oxalate salt.

The invention also relates to the use of a crystalline form of 4'-{2-ethoxy-4-ethyl-5-[((S)-2-mercapto-4-methylpentanoylamino)methyl]imidazol-1-ylmethyl}-3'-fluorobiphenyl-2-carboxylic acid for the manufacture of a medicament. Additionally, the invention relates to the use of a crystalline form of 4'-{2-ethoxy-4-ethyl-5-[((S)-2-mercapto-4-methylpentanoylamino)methyl]imidazol-1-ylmethyl}-3'-fluorobiphenyl-2-carboxylic acid for the manufacture of a medicament; especially for the manufacture of a medicament for the treatment of hypertension or heart failure. In specific embodiments, the crystalline form is a hemiedisylate salt form I, hemiedisylate salt form II, heminapadisylate salt, or mono-oxalate salt.

BRIEF DESCRIPTION OF THE DRAWINGS

Various aspects of the present invention are illustrated by reference to the accompanying drawings.

DETAILED DESCRIPTION OF THE INVENTION

Figure 1:
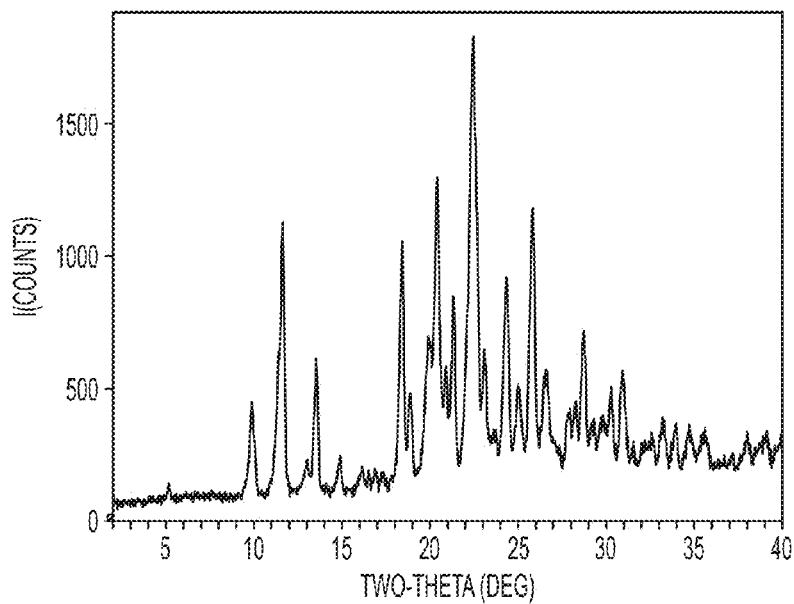
FIG. 1 shows a powder x-ray diffraction (PXRD) pattern of the crystalline hemiedisylate salt form I of the compound of formula I. The crystalline hemiedisylate salt form I is also characterized by a differential scanning calorimetry (DSC) thermogram in FIG. 2, a thermal gravimetric analysis (TGA) trace in FIG. 3, and a dynamic moisture sorption (DMS) profile in FIG. 4.

This invention provides crystalline forms of 4'-{2-ethoxy-4-ethyl-5-[((S)-2-mercapto-4-methylpentanoylamino)methyl]imidazol-1-ylmethyl}-3'-fluorobiphenyl-2-carboxylic acid. The active agent (i.e., the compound of formula I) contains one chiral center having the (S) configuration. However, it will be understood by those skilled in the art that minor amounts of the (R) stereoisomer may be present in the compositions of the invention unless otherwise indicated, provided that the utility of the composition as a whole is not eliminated by the presence of such an isomer. In addition, since the compound of formula I contains both a basic moiety (imidazole), and an acidic moiety (carboxylic acid), it may exist as a zwitterion.

The compound of formula I has $AT_1$ receptor antagonist activity and NEP inhibition activity. Crystalline forms of the compound of formula I are expected to have the same activity, and thus the same utility in treating diseases such as hypertension and heart failure. Therefore, among other uses, the crystalline forms of the invention are useful for preparing pharmaceutical compositions for treating hypertension or heart failure.

DEFINITIONS

When describing the compounds, compositions, methods and processes of the invention, the following terms have the following meanings unless otherwise indicated. Additionally, as used herein, the singular forms "a," "an" and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

As used herein, the phrase "having the formula" or "having the structure" is not intended to be limiting and is used in the same way that the term "comprising" is commonly used.

The term "hemi" as used herein is intended to mean that the crystalline form typically contains about 1.0 molar equivalents of freebase (the compound of formula I) per about 0.5±0.15 molar equivalent of counterion; and in one embodiment, about 1.0 molar equivalents of freebase per about 0.5 molar equivalent of counterion. Thus, the hemiedisylate forms (form I and form II) generally contain about 1.0 molar equivalents of freebase per about 0.5±0.15 molar equivalent of 1,2-ethanedisulfonic acid; and in one embodiment, about 1.0 molar equivalents of freebase per about 0.5 molar equivalent of 1,2-ethanedisulfonic acid. Similarly, the heminapadisylate form generally contains about 1.0 molar equivalents of freebase per about 0.5±0.15 molar equivalent of naphthalene-1,5-disulfonic acid; and in one embodiment, about 1.0 molar equivalents of freebase per about 0.5 molar equivalent of naphthalene-1,5-disulfonic acid.

The term "hydrate" means a crystal form, where molecules of water are incorporated in the unit cell of the crystal lattice. The hydrate may include one or more molecules of water, but the number of water molecules may also be a fraction of one, such as one-half or one-fourth. In the present invention, the heminapadisylate form is a hydrate and generally contains about 1.0 molar equivalent of freebase per about 0.5±0.15 molar equivalent of naphthalene-1,5-disulfonic acid and about 0.55±0.45 molar equivalent of water. In one embodiment, the heminapadisylate form contains about 1.0 molar equivalents of freebase per about 0.5±0.15 molar equivalent of naphthalene-1,5-disulfonic acid and about 0.25±0.15 molar equivalent of water; and in another embodiment, the heminapadisylate form contains about 1.0 molar equivalents of freebase per about 0.5 molar equivalent of naphthalene-1,5-disulfonic acid and about 0.25±0.15 molar equivalent of water.

The term "mono" as used herein is intended to mean that the crystalline form typically contains about 1.0 molar equivalents of freebase (the compound of formula I) per about 1.0±0.15 molar equivalent of counterion; and in one embodiment, about 1.0 molar equivalents of freebase per about 1.0 molar equivalent of counterion. Thus the crystalline monooxalate salt generally contains about 1.0 molar equivalents of freebase per about 1.0±0.15 molar equivalent of oxalic acid; and in one embodiment, about 1.0 molar equivalents of freebase per about 1.0 molar equivalent oxalic acid.

The term "melting point" or "melting endotherm" as used herein means the temperature at which the maximum endothermic heat flow is observed by differential scanning calorimetry, for the thermal transition that corresponds to the solid-to-liquid phase change.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

The term "therapeutically effective amount" means an amount sufficient to effect treatment when administered to a patient in need thereof, i.e., the amount of drug needed to obtain the desired therapeutic effect. For example, a therapeutically effective amount for treating hypertension is an amount of compound needed to, for example, reduce, suppress, eliminate or prevent the symptoms of hypertension, or to treat the underlying cause of hypertension. In one embodiment, a therapeutically effective amount is that amount needed to reduce blood pressure or the amount of drug needed to maintain normal blood pressure. On the other hand, the term "effective amount" means an amount sufficient to obtain a desired result, which may not necessarily be a therapeutic result. For example, when studying a system comprising an $AT_1$ receptor, an "effective amount" may be the amount needed to antagonize the receptor.

The term "treating" or "treatment" as used herein means the treating or treatment of a disease or medical condition (such as hypertension) in a patient, such as a mammal (particularly a human) that includes: (a) preventing the disease or medical condition from occurring, that is, prophylactic treatment of a patient; (b) ameliorating the disease or medical condition such as by eliminating or causing regression of the disease or medical condition in a patient; (c) suppressing the disease or medical condition such as by slowing or arresting the development of the disease or medical condition in a patient; or (d) alleviating the symptoms of the disease or medical condition in a patient. For example, the term "treating hypertension" would include preventing hypertension from occurring, ameliorating hypertension, suppressing hypertension, and alleviating the symptoms of hypertension (for example, lowering blood pressure). The term "patient" is intended to include those mammals, such as humans, that are in need of treatment or disease prevention or that are presently being treated for disease prevention or treatment of a specific disease or medical condition. The term "patient" also includes test subjects in which compounds of the invention are being evaluated or test subjects being used in a assay, for example an animal model.

All other terms used herein are intended to have their ordinary meaning as understood by those of ordinary skill in the art to which they pertain.

General Synthetic Procedures

The crystalline compounds of the invention can be synthesized from readily available starting materials as described below and in the Examples. There are several methods that can be used to produce these crystalline compounds. It is noted, however, that the crystalline content as well as the habit of the crystals (size and shape) may vary, based partly upon the method of preparation, as well as on the solvent composition. The crystals have been observed as having a plate, block, and needle morphology.

It will be appreciated that while specific process conditions (i.e., crystallization temperatures, times, mole ratios of reactants, solvents, pressures, etc.) are given, other process conditions can also be used unless otherwise stated. In some instances, reactions or crystallizations were conducted at room temperature and no actual temperature measurement was taken. It is understood that room temperature can be taken to mean a temperature within the range commonly associated with the ambient temperature in a laboratory environment, and will typically be in the range of about 15° C. to about 30° C. In other instances, reactions or crystallizations were conducted at room temperature and the temperature was actually measured and recorded.

In general, the crystalline forms of the invention are prepared by first treating 4'-{2-ethoxy-4-ethyl-5-[((S)-2-mercapto-4-methylpentanoylamino)methyl]imidazol-1-ylmethyl}-3'-fluorobiphenyl-2-carboxylic acid (referred to herein as the "freebase") with the appropriate counterion, i.e., 1,2-ethanedisulfonic acid, napthalene-1,5-disulfonic acid, or oxalic acid.

The 4'-{2-ethoxy-4-ethyl-5-[((S)-2-mercapto-4-methylpentanoylamino)methyl]-imidazol-1-ylmethyl}-3'-fluorobiphenyl-2-carboxylic acid employed in the invention can be readily prepared from commercially available starting materials and reagents using the procedures described in the Examples, or using the procedures described in the commonly-assigned U.S. applications described in the Background section of this application.

To prepare a crystalline salt of this invention, the 4'-{2-ethoxy-4-ethyl-5-[((S)-2-mercapto-4-methylpentanoylamino)methyl]-imidazol-1-ylmethyl}-3'-fluorobiphenyl-2-carboxylic acid is typically contacted with about 0.45 to about 1.2 molar equivalents of the appropriate counterion. In one embodiment, about 1.0 to about 1.2 molar equivalents of 1,2-ethanedisulfonic acid are used; and in a particular embodiment, about 1.1 molar equivalents of 1,2-ethanedisulfonic acid are used. In another embodiment, about 1.0 to about 1.2 molar equivalents of napthalene-1,5-disulfonic acid are used; and in a particular embodiment, about 1.1 molar equivalents of napthalene-1,5-disulfonic acid are used. In another embodiment, about 0.45 to about 0.65 molar equivalents of napthalene-1,5-disulfonic acid are used; and in a particular embodiment, about 0.55 molar equivalents of napthalene-1,5-disulfonic acid are used. In yet another embodiment, about 0.9 to about 1.1 molar equivalents of oxalic acid are used; and in a particular embodiment, about 1.0 molar equivalents of oxalic acid are used. The molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio.

Generally, crystallization is conducted in a suitable inert diluent or solvent system, examples of which include, but are not limited to, alcohols (e.g., methanol, ethanol, isopropanol, and isobutanol), ethyl acetate, acetonitrile, dichloromethane, methyl t-butyl ether, tetrahydrofuran, and the like, and mixtures thereof, and may optionally contain water. Crystallization of the hemiedisylate salt form I can be conducted using an alcohol (e.g., methanol or ethanol) and methyl t-butyl ether.

In one embodiment crystallization of the hemiedisylate salt form II can be conducted using an alcohol (e.g., ethanol) and methyl t-butyl ether. In another embodiment crystallization of the hemiedisylate salt form II can be conducted using an alcohol (e.g., ethanol), methyl t-butyl ether, water and ethyl acetate. In yet another embodiment crystallization of the hemiedisylate salt form II can be conducted using an alcohol (e.g., ethanol), water and ethyl acetate.

Crystallization of the heminapadisylate salt can be conducted using an alcohol (e.g., ethanol) and ethyl acetate, optionally including water.

Crystallization of the mono-oxalate salt can be conducted using acetonitrile, tetrahydrofuran and ethyl acetate.

Generally, crystallization is conducted at room temperature. However, it may be desired to gently heat (for example, ~30-80° C., more typically ~30-60° C.), stir, or sonicate the mixture to aid dissolution. The mixture is then allowed to stand to allow solids to form, which are then isolated to yield the crystalline form. Generally, solids will form at room temperature. However, the mixture may be cooled during this step, for example cooled to ~20-30° C.

After a suitable amount of time, crystals will be observed. Once crystals are observed, the volume of the mother liquor can be reduced and the crystals isolated and dried. Isolation of the solids from the reaction mixture can be accomplished by any conventional means such as precipitation, filtration, concentration, centrifugation, dried under vacuum, and the like.

The solids may also be washed with an inert diluent. In one embodiment, the solids are washed with ethanol, dioxane, or ethyl acetate.

After the initial crystallization, subsequent work-up procedures may include a seed crystal to facilitation crystallization.

Crystalline Properties

Among other advantages, it has been discovered that forming crystalline forms of the compound of formula I, is useful for purifying the compound itself. For example, the crystalline forms of the invention have purities in the range of 98-99%

As is well known in the field of powder x-ray diffraction, relative peak heights of PXRD patterns are dependent on a number of factors relating to sample preparation and instrument geometry, while peak positions are relatively insensitive to experimental details. PXRD patterns and differential scanning calorimetry (DSC) thermograms were obtained, and thermogravimetric analysis (TGA) and dynamic moisture sorption (DMS) assessment (also known as a moisture sorption-desorption profile) were performed as described in Example 9. Thus, in one embodiment, the crystalline compounds of the invention are characterized by a PXRD pattern having certain peak positions. In another embodiment, the crystalline compounds of the invention are characterized by a DSC thermogram. In yet another embodiment, the crystalline compounds of the invention are characterized by a TGA trace. In another embodiment, the crystalline compounds of the invention are characterized by a polarized light microscopic (PLM) image.

Hemiedisylate Salt Form I

The crystalline hemiedisylate salt form I is characterized by a PXRD pattern in which the peak positions are substantially in accordance with those shown in FIG. 1. Those peaks are listed below. Only peaks having a relative peak height (H %) of about 15% or greater are listed.

| 2θ | d (Å) | Height[1] | H %[2] | * |
|---|---|---|---|---|
| 9.89 | 8.94 | 358 | 22.9 | * |
| 11.66 | 7.59 | 1013 | 64.7 | * |
| 13.55 | 6.53 | 495 | 31.6 | * |
| 18.41 | 4.82 | 898 | 57.3 | * |
| 18.89 | 4.69 | 302 | 19.3 | |
| 19.91 | 4.46 | 512 | 32.7 | |
| 20.42 | 4.35 | 1101 | 70.3 | * |
| 20.90 | 4.25 | 356 | 22.8 | |
| 21.33 | 4.16 | 508 | 32.4 | |
| 22.46 | 3.96 | 1566 | 100 | * |
| 24.35 | 3.65 | 637 | 40.7 | |
| 25.85 | 3.44 | 877 | 56 | |
| 28.73 | 3.10 | 372 | 23.8 | |
| 30.92 | 2.89 | 321 | 20.5 | |

[1]Peak height from base line
[2]Percent peak height compared to highest peak
*Indicates peaks that are important to identify this form Thus, in one embodiment, the crystalline hemiedisylate salt form I is characterized by a powder x-ray diffraction (PXRD) pattern comprising diffraction peaks at 2θ values of 9.89±0.20, 11.66±0.20, 13.55±0.20, 18.41±0.20, 20.42±0.20, and 22.46±0.20; and in another embodiment, is further characterized by having one or more additional diffraction peaks at 2θ values selected from 18.89±0.20, 19.91±0.20, 20.90±0.20, 21.33±0.20, 24.35±0.20, 25.85±0.20, 28.73±0.20, and 30.92±0.20.

Figure 2:
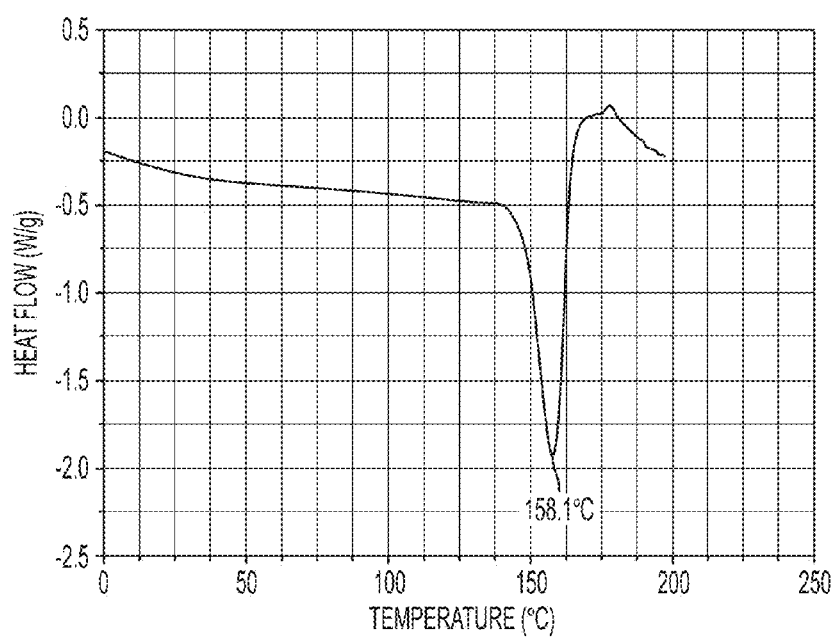

In one embodiment, the crystalline hemiedisylate salt form I is characterized by the DSC thermogram in FIG. 2. The DSC thermogram demonstrates that the crystalline hemiedisylate salt form I has excellent thermal stability with a melting point at about 158° C. and no significant thermal decomposition below 158° C. The non-complex thermal profile does not show any undesired endothermic or exothermic peak prior to the melting endotherm at 158° C., which suggests that this crystalline solid is most likely an anhydrous crystalline form.

Figure 3:
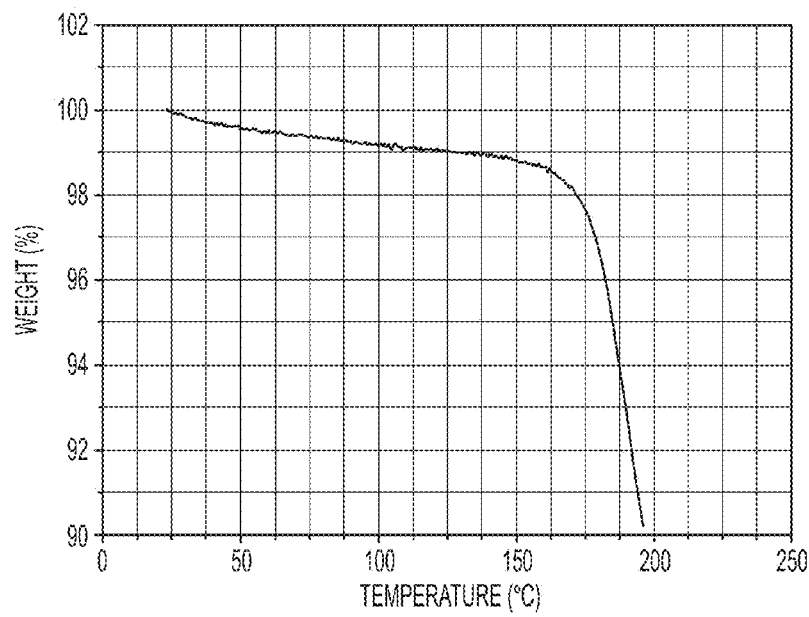

In one embodiment, the crystalline hemiedisylate salt form I is characterized by the TGA profile in FIG. 3. The TGA trace shows a small loss of solvents and/or water (about 1 wt %) at temperatures below about 125° C., which is consistent with the loss of residual moisture or solvent.

Figure 4:
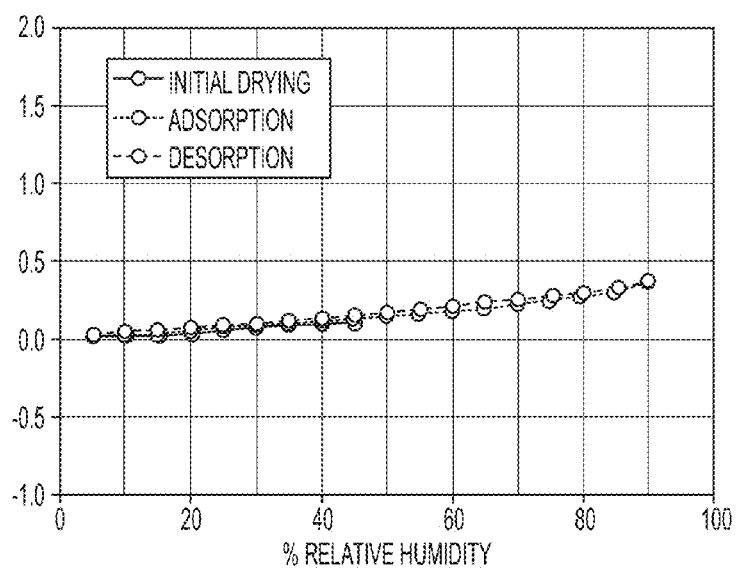

In one embodiment, the crystalline hemiedisylate salt form I is characterized by the DMS profile in FIG. 4. This DMS profile demonstrates that this form has a reversible sorption/desorption profile with acceptable levels of hygroscopicity. This crystalline form has a small weight gain (about 0.38%) when it exposed to a broad humidity range from 5% RH up to 90% RH, and less than about 0.26% weight gain when exposed to up to 70% RH. This suggests that the crystalline hemiedisylate form I possesses only a minimal risk of hygroscopicity at ambient conditions.

Figure 5:
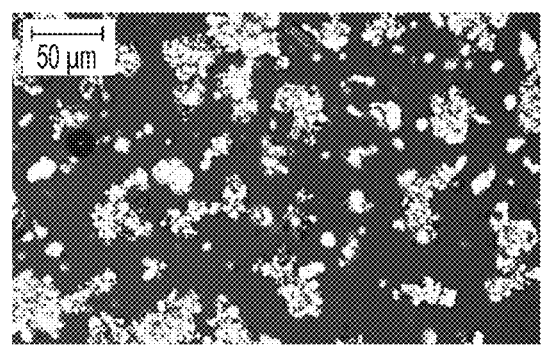
FIG. 5 is a polarized light microscopic (PLM) image of the crystalline hemiedisylate salt form I.

In another embodiment, the crystalline hemiedisylate salt form I is characterized by the PLM image in FIG. 5.

Hemiedisylate Form II

Figure 6:
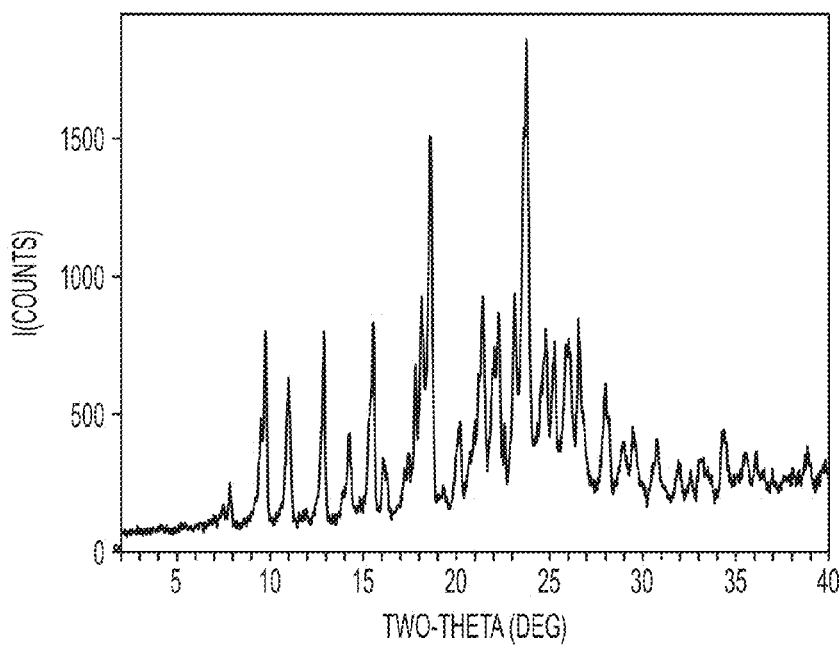
FIG. 6 shows a PXRD pattern of the crystalline hemiedisylate salt form II of the compound of formula I. The crystalline hemiedisylate salt form II is also characterized by a DSC thermogram in FIG. 7, a TGA trace in FIG. 8, and a DMS profile in FIG. 9.

The crystalline hemiedisylate salt form II is characterized by a PXRD pattern in which the peak positions are substantially in accordance with those shown in FIG. 6. Those peaks are listed below. Only peaks having a relative peak height (H %) of about 15% or greater are listed.

| 2θ | d (Å) | Height[1] | H %[2] | * |
|---|---|---|---|---|
| 9.74 | 9.07 | 688 | 46.3 | * |
| 11.00 | 8.04 | 519 | 34.9 | * |
| 12.89 | 6.86 | 684 | 46 | * |
| 14.27 | 6.20 | 289 | 19.4 | * |
| 15.54 | 5.70 | 684 | 46.1 | * |
| 17.81 | 4.98 | 525 | 35.3 | |
| 18.14 | 4.89 | 710 | 47.8 | |
| 18.62 | 4.76 | 1276 | 85.9 | * |
| 21.44 | 4.14 | 582 | 39.2 | |
| 22.25 | 3.99 | 535 | 36 | |
| 23.15 | 3.84 | 608 | 41 | |
| 23.78 | 3.74 | 1485 | 100 | * |
| 24.80 | 3.59 | 400 | 26.9 | |
| 25.28 | 3.52 | 374 | 25.2 | |
| 26.03 | 3.42 | 413 | 27.8 | |
| 26.58 | 3.35 | 535 | 36 | |
| 28.01 | 3.18 | 371 | 25 | |

[1]Peak height from base line
[2]Percent peak height compared to highest peak
*Indicates peaks that are important to identify this form Thus, in one embodiment, the crystalline hemiedisylate salt form II is characterized by a powder x-ray diffraction (PXRD) pattern comprising diffraction peaks at 2θ values of 9.74±0.20, 11.00±0.20, 12.89±0.20, 14.27±0.20, 15.54±0.20, 18.62±0.20, and 23.78±0.20; and in another embodiment, is further characterized by having one or more additional diffraction peaks at 2θ values selected from 17.81±0.20, 18.14±0.20, 21.44±0.20, 22.25±0.20, 23.15±0.20, 24.80±0.20, 25.28±0.20, 26.03±0.20, 26.58±0.20, and 28.01±0.20.

Figure 7:
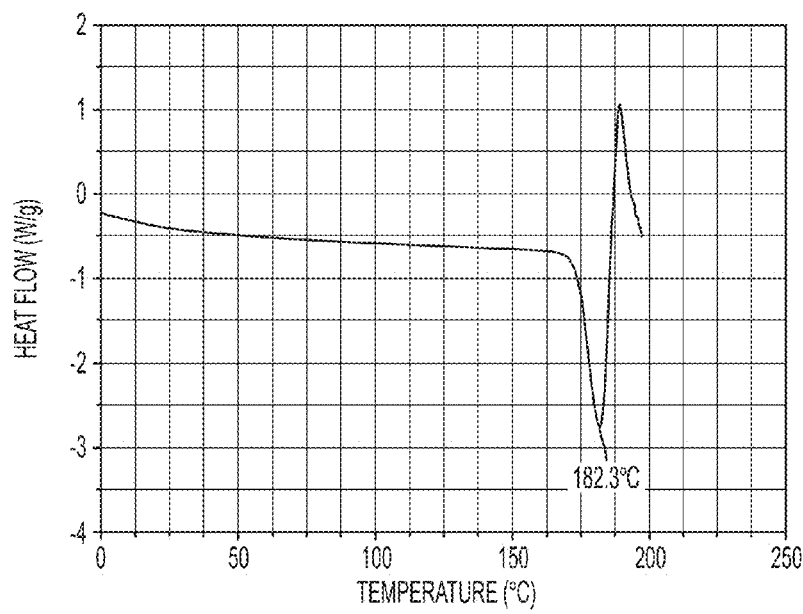

In one embodiment, the crystalline hemiedisylate salt form II is characterized by the DSC thermogram in FIG. 7. The DSC thermogram demonstrates that the crystalline hemiedisylate salt form II has excellent thermal stability with a melting point at about 182° C. and no significant thermal decomposition below 182° C. The non-complex thermal profile does not show any undesired endothermic or exothermic peak prior to the melting endotherm at 182° C., which suggests that this crystalline solid is most likely an anhydrous crystalline form.

Figure 8:
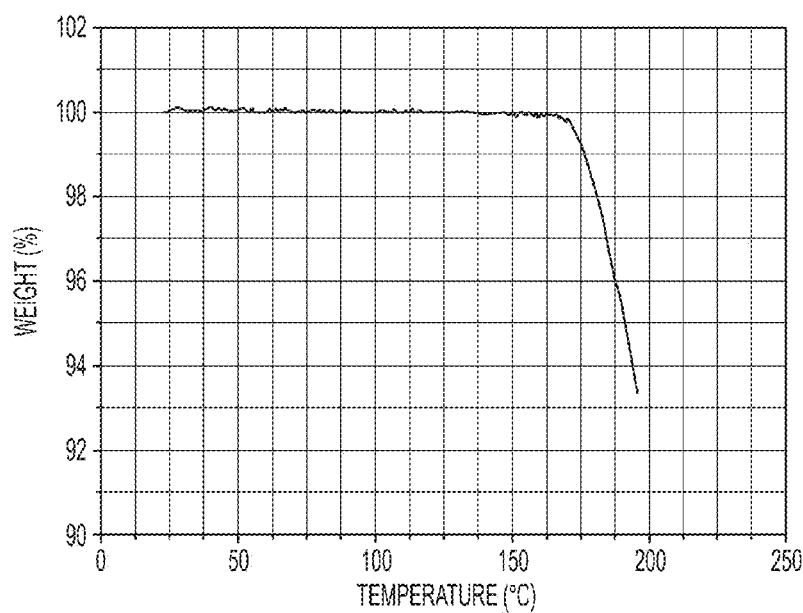

In one embodiment, the crystalline hemiedisylate salt form II is characterized by the TGA profile in FIG. 8. The TGA trace shows no loss of solvents and/or water at temperatures below about 180° C., indicating the phase purity of the anhydrous material.

Figure 9:
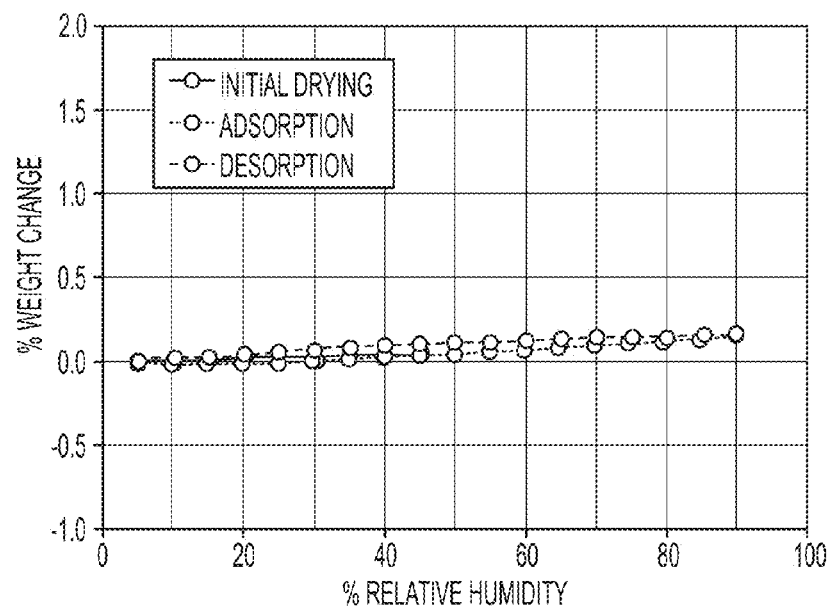

In one embodiment, the crystalline hemiedisylate salt form II is characterized by the DMS profile in FIG. 9. This DMS profile demonstrates that this form has a reversible sorption/desorption profile with acceptable levels of hygroscopicity. This crystalline form has an insignificant weight gain (about 0.16%) when it exposed to a broad humidity range from 5% RH up to 90% RH, and less than about 0.10% weight gain when exposed to up to 70% RH. This suggests that the crystalline hemiedisylate salt form II possesses only a minimal risk of hygroscopicity at ambient conditions.

Figure 10:
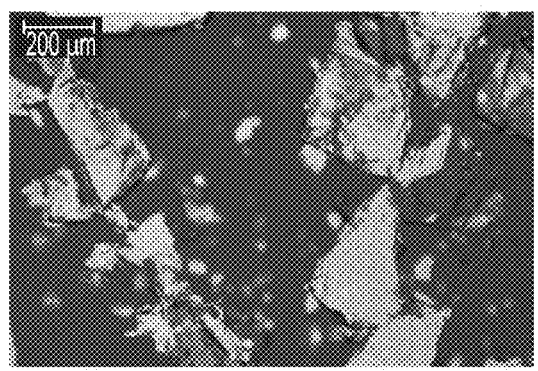
FIG. 10 is a PLM image of the crystalline hemiedisylate salt form II.

In another embodiment, the crystalline hemiedisylate salt form II is characterized by the PLM image in FIG. 10.

Heminapadisylate Salt

Figure 11:
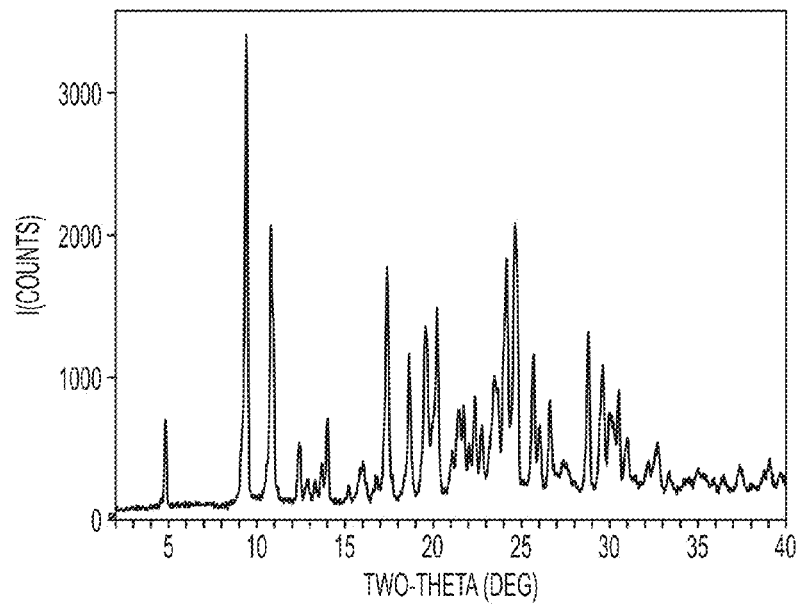
FIG. 11 shows a PXRD pattern of the crystalline heminapadisylate salt of the compound of formula I. The crystalline heminapadisylate salt is also characterized by a DSC thermogram in FIG. 12, a TGA trace in FIG. 13, and a DMS profile in FIG. 14.

The crystalline heminapadisylate salt is characterized by a PXRD pattern in which the peak positions are substantially in accordance with those shown in FIG. 11. Those peaks are listed below. Only peaks having a relative peak height (H %) of about 15% or greater are listed.

| 2θ | d (Å) | Height[1] | H %[2] | * |
|---|---|---|---|---|
| 4.84 | 18.25 | 612 | 18.7 | * |
| 9.41 | 9.39 | 3273 | 100 | * |
| 10.82 | 8.17 | 1919 | 58.6 | * |
| 14.05 | 6.30 | 565 | 17.3 | |
| 17.39 | 5.10 | 1623 | 49.6 | * |
| 18.65 | 4.75 | 986 | 30.1 | |
| 19.55 | 4.54 | 1168 | 35.7 | |
| 20.21 | 4.39 | 1270 | 38.8 | |
| 21.44 | 4.14 | 563 | 17.2 | |
| 23.48 | 3.79 | 517 | 15.8 | |
| 24.17 | 3.68 | 1581 | 48.3 | * |
| 24.65 | 3.61 | 1826 | 55.8 | * |
| 25.69 | 3.46 | 908 | 27.7 | |
| 26.65 | 3.34 | 564 | 17.2 | |
| 28.79 | 3.10 | 1096 | 33.5 | |
| 29.63 | 3.01 | 785 | 24 | |
| 30.52 | 2.93 | 502 | 15.3 | |

[1]Peak height from base line
[2]Percent peak height compared to highest peak
*Indicates peaks that are important to identify this form Thus, in one embodiment, the crystalline heminapadisylate salt is characterized by a powder x-ray diffraction (PXRD) pattern comprising diffraction peaks at 2θ values of 4.84±0.20, 9.41±0.20, 10.82±0.20, 17.39±0.20, 24.17±0.20, and 24.65±0.20; and in another embodiment, is further characterized by having one or more additional diffraction peaks at 2θ values selected from 14.05±0.20, 18.65±0.20, 19.55±0.20, 20.21±0.20, 21.44±0.20, 23.48±0.20, 25.69±0.20, 26.65±0.20, 28.79±0.20, 29.63±0.20, and 30.52±0.20.

Figure 12:
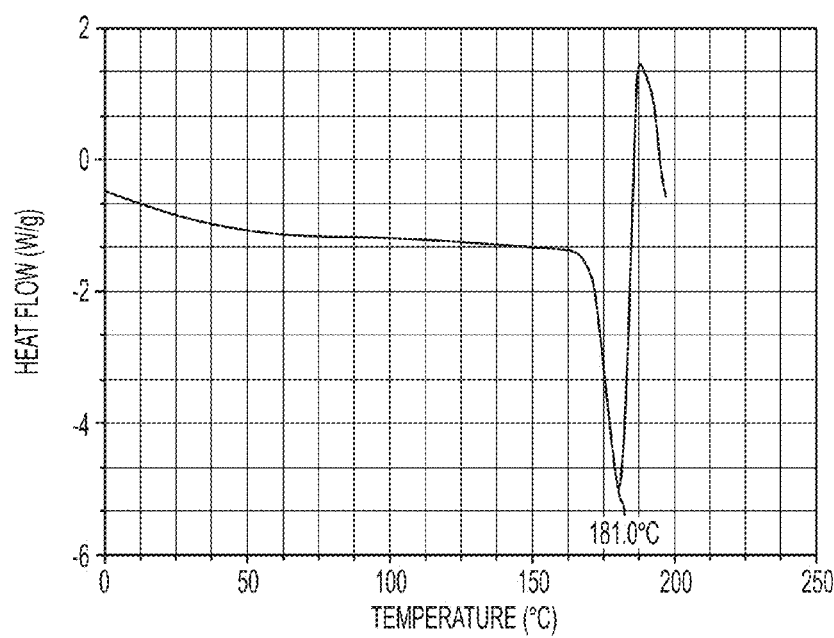

In one embodiment, the crystalline heminapadisylate salt is characterized by the DSC thermogram in FIG. 12. The DSC thermogram demonstrates that the crystalline heminapadisylate form has excellent thermal stability with a melting point at about 181° C. and no significant thermal decomposition below 181° C. The thermal profile appears to show a shallow endothermic peak below 100° C., which may correspond to small quantities of solvent that are contained within the crystalline lattice or adsorbed on the crystalline surface.

Figure 13:
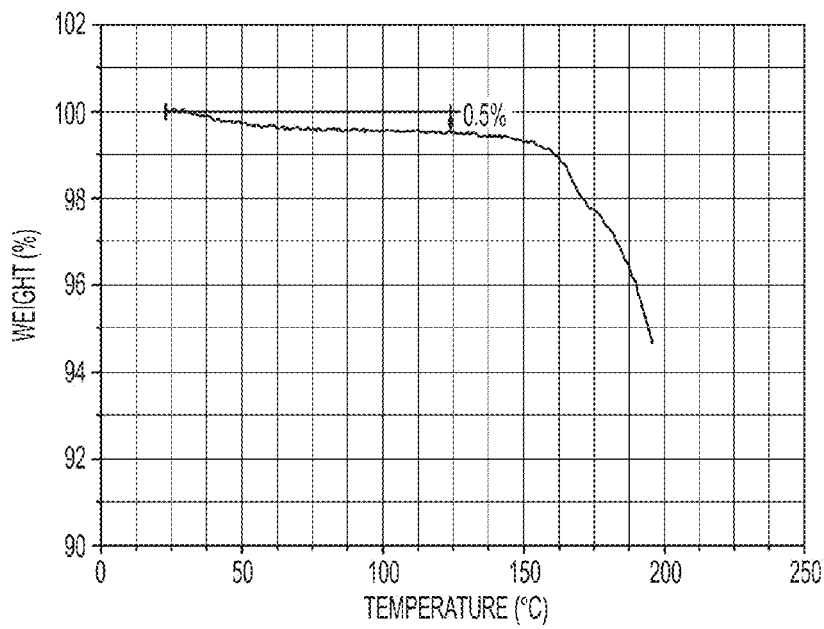

In one embodiment, the crystalline heminapadisylate salt is characterized by the TGA profile in FIG. 13. The TGA trace shows a small loss of solvents and/or water (about 0.5 wt %) at temperatures below about 125° C., which is consistent with the loss of residual or lattice-included moisture or solvent.

Figure 14:
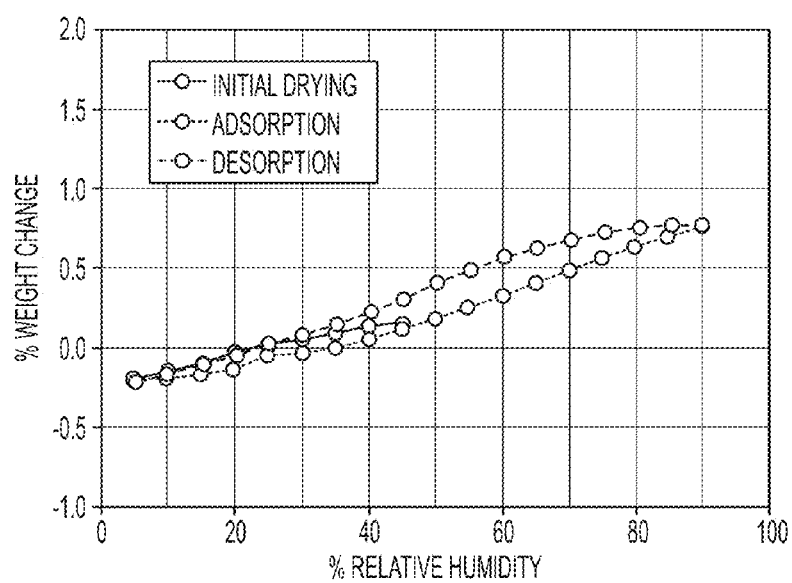

In one embodiment, the crystalline heminapadisylate salt is characterized by the DMS profile in FIG. 14. This DMS profile demonstrates that this form has a reversible sorption/desorption profile with acceptable levels of hygroscopicity. This crystalline form has a small weight gain (about 0.97%) when it exposed to a broad humidity range from 5% RH up to 90% RH, and less than about 0.68% weight gain when exposed to up to 70% RH. This suggests that the crystalline heminapadisylate salt possesses only a minimal risk of hygroscopicity at ambient conditions.

The crystalline heminapadisylate salt has been further characterized by x-ray diffraction analysis of crystal structure, providing the following lattice parameters: unit cell is triclinic with dimensions a=9.199(1) Å, b=10.556(1) Å, c=19.348(3) 521; α=80.754(8°), β=79.286(7°), γ=66.111 (6°), space group is P1bar; calculated density is 1.337 g/cm$^3$. The resulting crystal structure confirms that the chemical composition of the compound is that of formula I and that the unit contains two symmetry independent {2-ethoxy-4-ethyl-5-[((S)-2-mercapto-4-methylpentanoylamino)methyl]imidazol-1-ylmethyl}-3'-fluorobiphenyl-2-carboxylic acid molecules, one naphthalenedisulfonate anion, and approximately half molecule of water leading to the determination that this crystal is a hydrate. Powder x-ray diffraction peaks calculated from the derived atomic positions are in excellent agreement with observed results.

Figure 15:
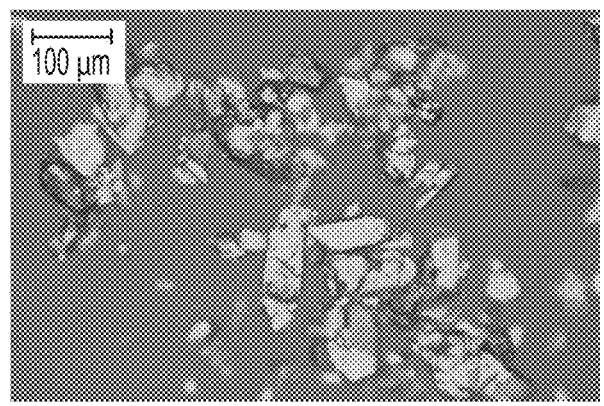
FIG. 15 is a PLM image of the crystalline heminapadisylate salt.

In another embodiment, the crystalline heminapadisylate salt is characterized by the PLM image in FIG. 15.

Mono-Oxalate Salt

Figure 17:
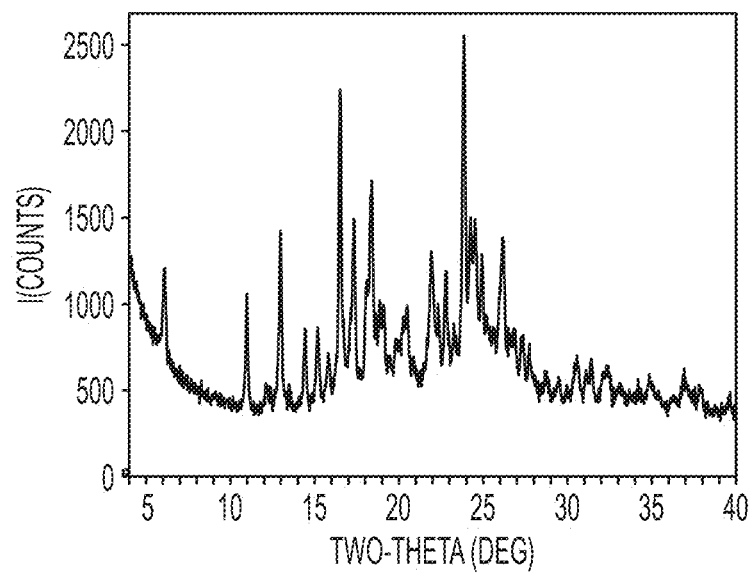
FIG. 17 shows a PXRD pattern of the crystalline mono-oxalate salt of the compound of formula I. The crystalline mono-oxalate salt is also characterized by a DSC thermogram in FIG. 18, a TGA trace in FIG. 19, and a DMS profile in FIG. 20.

The crystalline mono-oxalate salt is characterized by a PXRD pattern in which the peak positions are substantially in accordance with those shown in FIG. 17. Those peaks are listed below. Only peaks having a relative peak height (H %) of about 10% or greater are listed. Sharp diffraction peaks in the region 5-40° in 2θ indicate the presence of crystalline material. Broad halo in the region 15-30° in 2θ corresponds to some of the uncrystallized amorphous content in the material.

| 2θ | d (Å) | Height[1] | H %[2] | * |
|---|---|---|---|---|
| 6.1 | 14.4 | 484 | 27.9 | * |
| 11.0 | 8.1 | 662 | 38.2 | * |
| 13.0 | 6.8 | 999 | 57.6 | * |
| 14.4 | 6.1 | 429 | 24.7 | * |
| 15.2 | 5.8 | 405 | 23.4 | * |
| 15.8 | 5.6 | 213 | 12.3 | |
| 16.5 | 5.4 | 1690 | 97.4 | * |
| 17.3 | 5.1 | 856 | 49.4 | * |
| 18.1 | 4.9 | 466 | 26.9 | |
| 18.4 | 4.8 | 1107 | 63.9 | * |
| 19.1 | 4.6 | 230 | 13.2 | |
| 20.3 | 4.4 | 318 | 18.4 | |
| 20.5 | 4.3 | 396 | 22.9 | |
| 21.9 | 4.1 | 669 | 38.6 | * |
| 22.3 | 4.0 | 355 | 20.5 | |
| 22.8 | 3.9 | 488 | 28.1 | |
| 23.9 | 3.7 | 1734 | 100.0 | * |
| 24.3 | 3.7 | 705 | 40.7 | * |
| 24.5 | 3.6 | 712 | 41.0 | * |
| 24.9 | 3.6 | 372 | 21.4 | |
| 26.1 | 3.4 | 656 | 37.8 | * |
| 27.4 | 3.3 | 227 | 13.1 | |
| 27.8 | 3.2 | 218 | 12.5 | |
| 30.6 | 2.9 | 228 | 13.1 | |
| 31.4 | 2.8 | 211 | 12.2 | |
| 36.9 | 2.4 | 219 | 12.6 | |

[1]Peak height from base line
[2]Percent peak height compared to highest peak
*Indicates peaks that are important to identify this form Thus, in one embodiment, the crystalline mono-oxalate salt is characterized by a powder x-ray diffraction (PXRD) pattern comprising diffraction peaks at 2θ values of 6.1±0.20, 11.0±0.20, 13.0±0.20, 14.4±0.20, 15.2±0.20, 16.5±0.20, 17.3±0.20, 18.4±0.20, 21.9±0.20, 23.9±0.20, 24.3±0.20, 24.5±0.20, and 26.1±0.20; and in another embodiment, is further characterized by having one or more additional diffraction peaks at 2θ values selected from 15.8±0.20, 18.1±0.20, 19.1±0.20, 20.3±0.20, 20.5±0.20, 22.3±0.20, 22.8±0.20, 24.9±0.20, 27.4±0.20, 27.8±0.20, 30.6±0.20, 31.4±0.20, and 36.9±0.20.

Figure 18:
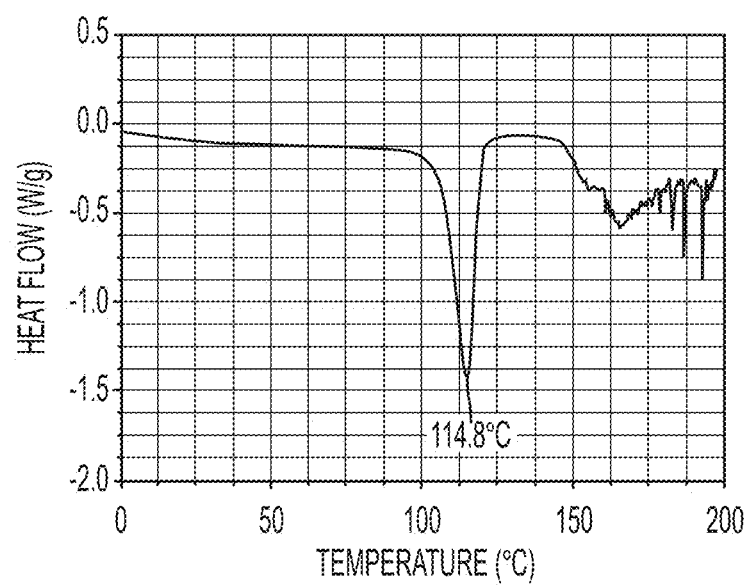

In one embodiment, the crystalline mono-oxalate salt is characterized by the DSC thermogram in FIG. 18. The DSC thermogram demonstrates that the crystalline mono-oxalate salt has excellent thermal stability with a melting point at about 115° C. No other thermal events were observed prior to the melting transition and no significant thermal decomposition was observed below 140° C.

Figure 19:
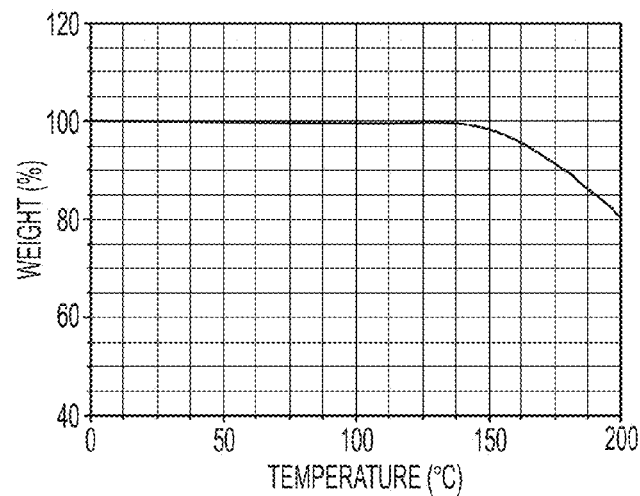

In one embodiment, the crystalline mono-oxalate salt is characterized by the TGA profile in FIG. 19. The TGA trace shows no mass loss prior to or during melting. The material decomposes after 140° C., as evidenced by significant weight loss in the TGA trace.

Figure 20:
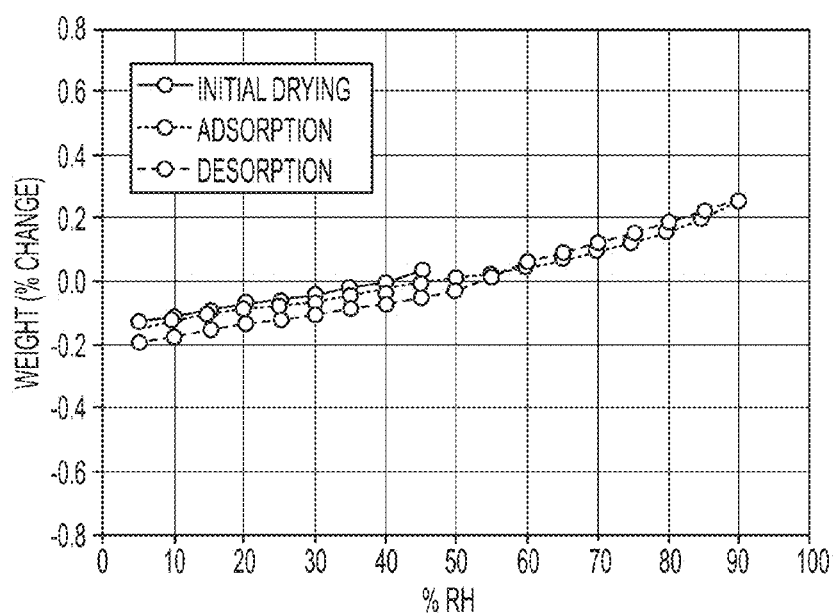

In one embodiment, the crystalline mono-oxalate salt is characterized by the DMS profile in FIG. 20. This DMS profile demonstrates that during the adsorption segment, the material picks up moisture gradually from 5% RH to 90% RH, and loses the moisture during drying segment. The moisture is most likely taken up by the amorphous content within the material. After the solid was subjected to moisture sorption and desorption segments, the solid remained as the known anhydrous form, as confirmed by powder X-ray diffraction analysis and differential scanning calorimetry.

Figure 21:
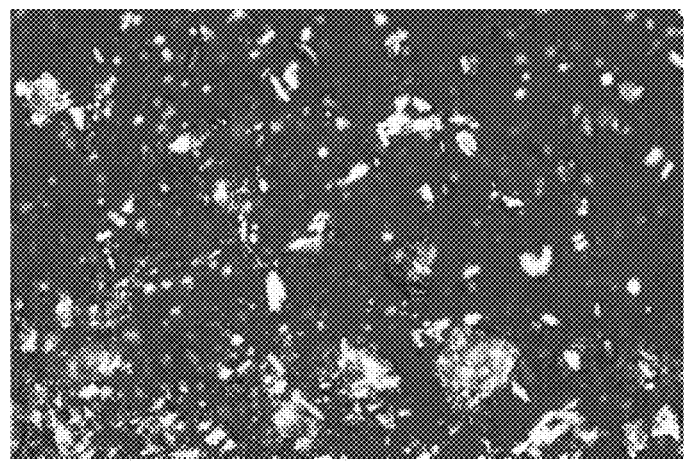
FIG. 21 is a PLM image of the crystalline mono-oxalate salt.

In another embodiment, the crystalline mono-oxalate salt is characterized by the PLM image in FIG. 21, which shows the material as being birefringent.

Utility

The compound of formula I possesses angiotensin II type 1 (AT$_1$) receptor antagonist activity and neprilysin (NEP) inhibition activity, i.e., the compound is able to inhibit enzyme-substrate activity. One measure of the affinity of a compound for the AT$_1$ receptor is the inhibitory constant (K$_i$) for binding to the AT$_1$ receptor. The pK$_i$ value is the negative logarithm to base 10 of the K$_i$. One measure of the ability of a compound to inhibit NEP activity is the inhibitory concentration (IC$_{50}$), which is the concentration of compound that results in half-maximal inhibition of substrate conversion by the NEP enzyme. The $pIC_{50}$ value is the negative logarithm to base 10 of the $IC_{50}$. The compound of formula I exhibits a $pK_i$ at the $AT_1$ receptor greater than or equal to about 7.0, and exhibits a $pIC_{50}$ for NEP greater than or equal to about 7.0.

Exemplary assays to determine properties of the compound of formula I as well as of the crystalline forms of the invention, such as $AT_1$ receptor binding and/or NEP inhibiting activity, are described in U.S. Publication Nos. 2008/0269305 and 2009/0023228, both to Allegretti et al., and include by way of illustration and not limitation assays that measure $AT_1$ and $AT_2$ binding and NEP inhibition. Useful secondary assays include: an assay to measure angiotensin converting enzyme (ACE) inhibition; an assay to measure aminopeptidase P (APP) inhibition; and a pharmacodynamic assay to assess the in vivo inhibitory potencies for ACE, $AT_1$, and NEP in anesthetized rats (Seymour et al. *Hypertension* 7(Suppl I):I-35-I-42, 1985 and Wigle et al. *Can. J. Physiol. Pharmacol.* 70:1525-1528, 1992), where $AT_1$ inhibition is measured as the percent inhibition of the angiotensin II pressor response, ACE inhibition is measured as the percent inhibition of the angiotensin I pressor response, and NEP inhibition is measured as increased urinary cyclic guanosine 3',5'-monophosphate (cGMP) output. Useful in vivo assays include the conscious spontaneously hypertensive rat (SHR) model, a renin dependent hypertension model that is useful for measuring $AT_1$ receptor blocking (Intengan et al. (1999) *Circulation* 100(22):2267-2275 and Badyal et al. (2003) *Indian Journal of Pharmacology* 35:349-362), and the conscious desoxycorticosterone acetate-salt (DOCA-salt) rat model, a volume dependent hypertension model that is useful for measuring NEP activity (Trapani et al. (1989) *J. Cardiovasc. Pharmacol.* 14:419-424, Intengan et al. (1999) *Hypertension* 34(4):907-913, and Badyal et al. (2003) supra). Both the SHR and DOCA-salt models are useful for evaluating the ability of a test compound to reduce blood pressure. The DOCA-salt model is also useful to measure a test compound's ability to prevent or delay a rise in blood pressure. The compound of formula I as well as the crystalline forms of the invention are expected to antagonize the $AT_1$ receptor and inhibit the NEP enzyme in any of the assays listed above, or assays of a similar nature. Thus, the aforementioned assays are useful in determining the therapeutic utility of the crystalline forms of the invention, for example, their utility as antihypertensive agents. Other properties and utilities of the crystalline forms can be demonstrated using other in vitro and in vivo assays well-known to those skilled in the art.

Therefore, the crystalline forms of the compound of formula I are expected to find utility in the treatment and/or prevention of medical conditions responsive to $AT_1$ receptor antagonism and NEP inhibition. For example, by antagonizing the $AT_1$ receptor and thus interfering with the action of angiotensin II on its receptors, a crystalline form is expected to find utility in preventing the increase in blood pressure produced by angiotensin II, a potent vasopressor. In addition, by inhibiting NEP, a crystalline form is also expected to potentiate the biological effects of endogenous peptides that are metabolized by NEP, such as the natriuretic peptides, bombesin, bradykinins, calcitonin, endothelins, enkephalins, neurotensin, substance P and vasoactive intestinal peptide. For example, by potentiating the effects of the natriuretic peptides, the crystalline compound is expected to be useful to treat glaucoma. The crystalline forms of the invention are also expected to have other physiological actions, for example, on the renal, central nervous, reproductive and gastrointestinal systems.

The crystalline forms of the invention is expected to find utility in treating and/or preventing medical conditions such as cardiovascular and renal diseases. Cardiovascular diseases of particular interest include heart failure such as congestive heart failure, acute heart failure, chronic heart failure, and acute and chronic decompensated heart failure. Renal diseases of particular interest include diabetic nephropathy and chronic kidney disease. One embodiment of the invention is directed to a method for treating hypertension, comprising administering to a patient a therapeutically effective amount of a crystalline form of the invention. Typically, the therapeutically effective amount is the amount that is sufficient to lower the patient's blood pressure. In one embodiment, the crystalline form is administered as an oral dosage form.

Another embodiment of the invention is directed to a method for treating heart failure, comprising administering to a patient a therapeutically effective amount of a crystalline form of the invention. Typically, the therapeutically effective amount is the amount that is sufficient to lower blood pressure and/or improve renal functions. In one embodiment, the crystalline form is administered as an intravenous dosage form. When used to treat heart failure, the crystalline form may be administered in combination with other therapeutic agents such as diuretics, natriuretic peptides, and adenosine receptor antagonists.

The crystalline forms of the invention are also expected to be useful in preventative therapy, for example in preventing the progression of cardiac insufficiency after myocardial infarction, preventing arterial restenosis after angioplasty, preventing thickening of blood vessel walls after vascular operations, preventing atherosclerosis, and preventing diabetic angiopathy.

In addition, as a NEP inhibitor, the crystalline forms of the invention are expected to inhibit enkephalinase, which will inhibit the degradation of endogenous enkephalins and thus such compounds may also find utility as analgesics. Due to its NEP inhibition properties, the crystalline forms are also expected to be useful as antitussive agents and antidiarrheal agents (for example, for the treatment of watery diarrhea), as well as find utility in the treatment of menstrual disorders, preterm labor, pre-eclampsia, endometriosis, reproductive disorders (for example, male and female infertility, polycystic ovarian syndrome, implantation failure), and male and female sexual dysfunction, including male erectile dysfunction and female sexual arousal disorder. More specifically, the crystalline forms are expected to be useful in treating female sexual dysfunction, which is often defined as a female patient's difficulty or inability to find satisfaction in sexual expression. This covers a variety of diverse female sexual disorders including, by way of illustration and not limitation, hypoactive sexual desire disorder, sexual arousal disorder, orgasmic disorder and sexual pain disorder. When used to treat such disorders, especially female sexual dysfunction, a crystalline form may be combined with one or more of the following secondary agents: PDE5 inhibitors, dopamine agonists, estrogen receptor agonists and/or antagonists, androgens, and estrogens.

The amount of the crystalline form administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for other diseases and conditions described herein, are well known and are readily available to the treating physician. Continuous monitoring by the physician will insure that the optimal amount of the crystalline form will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Since the crystalline forms of the invention are expected to possess $AT_1$ receptor antagonist activity and NEP enzyme inhibition activity, they are also useful as research tools for investigating or studying biological systems or samples having $AT_1$ receptors or a NEP enzyme, for example to study diseases where the $AT_1$ receptor or NEP enzyme plays a role. Any suitable biological system or sample having $AT_1$ receptors and/or a NEP enzyme may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention an $AT_1$ receptor in a mammal is antagonized by administering an $AT_1$-antagonizing amount of a crystalline form. In another particular embodiment, NEP enzyme activity in a mammal is inhibited by administering a NEP-inhibiting amount of a crystalline form. The crystalline forms can also be used as research tools by conducting biological assays using such form.

When used as a research tool, a biological system or sample comprising an $AT_1$ receptor and/or a NEP enzyme is typically contacted with an $AT_1$ receptor-antagonizing or NEP enzyme-inhibiting amount of a crystalline form. After the biological system or sample is exposed to the crystalline form, the effects of antagonizing the $AT_1$ receptor and/or inhibiting the NEP enzyme are determined using conventional procedures and equipment, such as by measuring receptor binding in a binding assay or measuring ligand-mediated changes in a functional assay. Exposure encompasses contacting cells or tissue with the compound, administering the compound to a mammal, for example by i.p., i.v. or s.c. administration, and so forth. This determining step can involve measuring a response (a quantitative analysis) or can involve making an observation (a qualitative analysis). Measuring a response involves, for example, determining the effects of the crystalline form on the biological system or sample using conventional procedures and equipment, such as radioligand binding assays and measuring ligand-mediated changes in functional assays. The assay results can be used to determine the activity level as well as the amount of compound necessary to achieve the desired result, that is, an $AT_1$ receptor-antagonizing and/or a NEP enzyme-inhibiting amount. Typically, the determining step will involve determining the $AT_1$ receptor ligand-mediated effects and/or determining the effects of inhibiting the NEP enzyme.

Additionally, the crystalline forms of the invention can be used as research tools for evaluating other chemical compounds, and thus are also useful in screening assays to discover, for example, new compounds having $AT_1$ receptor-antagonizing activity and/or NEP-inhibiting activity. In this manner, a crystalline form is used as a standard in an assay to allow comparison of the results obtained with a test compound and with the crystalline form to identify those test compounds that have about equal or superior activity, if any. For example, $K_i$ data (as determined, for example, by a binding assay) for a test compound or a group of test compounds is compared to the $K_i$ data for a crystalline form to identify those test compounds that have the desired properties, for example, test compounds having a $K_i$ value about equal or superior to a crystalline form of the invention, if any. This aspect of the invention includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a crystalline form of the invention to provide a second assay value; wherein step (a) is conducted either before, after or concurrently with step (b); and (c) comparing the first assay value from step (a) with the second assay value from step (b). Exemplary biological assays include an $AT_1$ receptor binding assay and a NEP enzyme inhibition assay.

Pharmaceutical Compositions and Formulations

The crystalline forms of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. Further, a crystalline form may be administered, for example orally, in multiple doses per day (for example, two, three, or four times daily), in a single daily dose or a single weekly dose. It will be understood by those skilled in the art that, once the crystalline form has been formulated, it may no longer be in crystalline form, i.e., the c crystalline form may be dissolved in a suitable carrier.

Accordingly, in one embodiment, the invention relates to a pharmaceutical composition comprising a pharmaceutically acceptable carrier and a crystalline form of 4'-{2-ethoxy-4-ethyl-5-[((S)-2-mercapto-4-methylpentanoylamino)methyl] imidazol-1-ylmethyl}-3'-fluorobiphenyl-2-carboxylic acid. Such pharmaceutical compositions may also contain other therapeutic and/or formulating agents if desired. When discussing compositions, the "crystalline forms of the invention" may also be referred to herein as an "active agent" to distinguish it from other components of the formulation, such as the carrier.

The pharmaceutical compositions of the invention typically contain a therapeutically effective amount of a crystalline form. Those skilled in the art will recognize, however, that a pharmaceutical composition may contain more than a therapeutically effective amount, such as in bulk compositions, or less than a therapeutically effective amount, that is, individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

Since the crystalline forms of the invention contain a thiol group, additional consideration may be given to minimize or eliminate oxidation of the thiol to form a disulfide. In solid formulations, this may be accomplished by reducing the drying time, decreasing the moisture content of the formulation, and including anti-oxidants such as ascorbic acid, sodium ascorbate, sodium sulfite and sodium bisulfite, as well as materials such as a mixture of lactose and microcrystalline cellulose. In liquid formulations, stability of the thiol may be improved by the addition of amino acids, antioxidants, or a combination of disodium edetate and ascorbic acid.

In one embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (capsules, tablets, pills and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and anti-oxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in microencapsulated form, optionally with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (for example, cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, that is, each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's air-stream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, glycerin, and sodium lauryl sulfate. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

The crystalline forms of the invention can also be administered parenterally (for example, by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. Parenteral formulations may also contain one or more anti-oxidants, solubilizers, stabilizers, preservatives, wetting agents, emulsifiers, and dispersing agents. Surfactants, additional stabilizing agents or pH-adjusting agents (acids, bases or buffers) and anti-oxidants are particularly useful to provide stability to the formulation, for example, to minimize or avoid hydrolysis of ester and amide linkages, or dimerization of the thiol that is present in the compound. These formulations may be rendered sterile by use of a sterile injectable medium, a sterilizing agent, filtration, irradiation, or heat. In one particular embodiment, the parenteral formulation comprises an aqueous cyclodextrin solution as the pharmaceutically acceptable carrier. Suitable cyclodextrins include cyclic molecules containing six or more α-D-glucopyranose units linked at the 1,4 positions by a linkages as in amylase, β-cyclodextrin or cycloheptaamylose. Exemplary cyclodextrins include cyclodextrin derivatives such as hydroxypropyl and sulfobutyl ether cyclodextrins such as hydroxypropyl-β-cyclodextrin and sulfobutyl ether β-cyclodextrin. Exemplary buffers for such formulations include carboxylic acid-based buffers such as citrate, lactate and maleate buffer solutions.

The crystalline forms of the invention can also be administered transdermally using known transdermal delivery systems and excipients. For example, the compound can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

If desired, the crystalline forms of the invention may be administered in combination with one or more other therapeutic agents. Thus, in one embodiment, pharmaceutical compositions of the invention contain other drugs that are co-administered with a crystalline form of the invention. For example, the composition may further comprise one or more therapeutic agents (also referred to as "secondary agents(s)") selected from the group of diuretics, $\beta_1$ adrenergic receptor blockers, calcium channel blockers, angiotensin-converting enzyme inhibitors, $AT_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, and combinations thereof. Such therapeutic agents are well known in the art, and examples are described below. By combining the crystalline compound of the invention with a secondary agent, triple therapy can be achieved; $AT_1$ receptor antagonist activity, NEP inhibition activity, and activity associated with the secondary agent (for example, $\beta_1$ adrenergic receptor blocker) can be achieved using only two active components. Since compositions containing two active components are typically easier to formulate than compositions containing three active components, such two-component compositions provide a significant advantage over compositions containing three active components. Accordingly, in yet another embodiment of the invention, a pharmaceutical composition comprises a crystalline compound of the invention, a second active agent, and a pharmaceutically acceptable carrier. Third, fourth etc. active agents may also be included in the composition. In combination therapy, the amount of a crystalline form that is administered, as well as the amount of secondary agents, may be less than the amount typically administered in monotherapy.

The crystalline forms of the invention may be physically mixed with the second active agent to form a composition containing both agents, or each agent may be present in separate and distinct compositions which are administered to the patient simultaneously or at separate times. For example, a crystalline form can be combined with a second active agent using conventional procedures and equipment to form a combination of active agents comprising a compound of the invention and a second active agent. Additionally, the active agents may be combined with a pharmaceutically acceptable carrier to form a pharmaceutical composition comprising a crystalline form of the invention, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the crystalline compound, ranging anywhere from concurrent with administration of the crystalline compound to about 24 hours post-dose. This is also referred to as sequential administration. Thus, a crystalline form of the invention can be orally administered simultaneously or sequentially with another active agent using two tablets, with one tablet for each active agent, where sequential may mean being administered immediately after administration of the crystalline compound or at some predetermined time later (for example, one hour later or three hours later). Alternatively, the combination may be administered by different routes of administration, that is, one orally and the other by inhalation.

In one embodiment of the invention, a kit comprises a first dosage form comprising a crystalline form of the invention and at least one additional dosage form comprising one or more of the secondary agents set forth herein, in quantities sufficient to carry out the methods of the invention. The first dosage form and the second (or third, etc,) dosage form together comprise a therapeutically effective amount of active agents for the treatment or prevention of a disease or medical condition in a patient.

Secondary agent(s), when included, are present in a therapeutically effective amount such that they are typically administered in an amount that produces a therapeutically beneficial effect when co-administered with a crystalline form of the invention. Suitable doses for these secondary agents administered in combination with a crystalline form are in the range of about 0.05 µg/day to about 100 mg/day. The secondary agent can be in the form of a pharmaceutically acceptable salt, solvate, optically pure stereoisomer, and so forth. The secondary agent may also be in the form of a prodrug, for example, a compound having a carboxylic acid group that has been esterified. Thus, secondary agents listed below are intended to include all such forms, and are commercially available or can be prepared using conventional procedures and reagents.

In one embodiment, a crystalline form of the invention is administered in combination with a diuretic. Representative diuretics include, but are not limited to: carbonic anhydrase inhibitors such as acetazolamide and dichlorphenamide; loop diuretics, which include sulfonamide derivatives such as acetazolamide, ambuside, azosernide, bumetanide, butazolamide, chloraminophenamide, clofenamide, clopamide, clorexolone, disulfamide, ethoxolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and Na$^+$ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg or 25 mg per day.

The crystalline forms of the invention may also be administered in combination with a $\beta_1$ adrenergic receptor blocker. Representative $\beta_1$ adrenergic receptor blockers include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof. In one particular embodiment, the $\beta_1$ adrenergic receptor blocker is selected from atenolol, bisoprolol, metoprolol, propranolol, sotalol, and combinations thereof.

In one embodiment, a crystalline form of the invention is administered in combination with a calcium channel blocker. Representative calcium channel blockers include, but are not limited to, amlodipine, anipamil, aranipine, barnidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexiline, prenylamine, ryosidine, semotiadil, terodiline, tiapamil, verapamil, and combinations thereof. In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof.

The crystalline forms of the invention can also be administered in combination with an angiotensin-converting enzyme (ACE) inhibitor. Representative ACE inhibitors include, but are not limited to, accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltopril, pentopril, perindopril, quinapril, quinaprilat, ramipril, ramiprilat, saralasin acetate, spirapril, temocapril, trandolapril, zofenopril, and combinations thereof. In a particular embodiment, the ACE inhibitor is selected from: benazepril, enalapril, lisinopril, ramipril, and combinations thereof.

In one embodiment, a crystalline form of the invention is administered in combination with an AT$_1$ receptor antagonist, also known as angiotensin II type 1 receptor blockers (ARBs). Representative ARBs include, but are not limited to, abitesartan, benzyllosartan, candesartan, candesartan cilexetil, elisartan, embusartan, enoltasosartan, eprosartan, fonsartan, forasartan, glycyllosartan, irbesartan, isoteoline, losartan, medoximil, milfasartan, olmesartan, opomisartan, pratosartan, ripisartan, saprisartan, saralasin, sarmesin, tasosartan, telmisartan, valsartan, zolasartan, and combinations thereof. In a particular embodiment, the ARB is selected from candesartan, eprosartan, irbesartan, losartan, olmesartan, irbesartan, saprisartan, tasosartan, telmisartan, and combinations thereof. Exemplary salts include eprosartan mesylate, losartan potassium salt, and olmesartan medoxomil. Typically, the ARB will be administered in an amount sufficient to provide from about 4-600 mg per dose, with exemplary daily dosages ranging from 20-320 mg per day.

In another embodiment, a crystalline form of the invention is administered in combination with a neprilysin (NEP) inhibitor. Representative NEP inhibitors include, but are not limited to: candoxatril; candoxatrilat; dexecadotril ((+)-N-[2 (R)-(acetylthiomethyl)-3-phenylpropionyl]glycine benzyl ester); CGS-24128 (3-[3-(biphenyl-4-yl)-2-(phosphonomethylamino)propionamido]propionic acid); CGS-24592 ((S)-3-[3-(biphenyl-4-yl)-2-(phosphonomethylamino)propionamido]propionic acid); CGS-25155 (N-[9(R)-(acetylthiomethyl)-10-oxo-1-azacyclodecan-2(S)-ylcarbonyl]-4(R)-hydroxy-L-proline benzyl ester); 3-(1-carbamoylcyclohexyl)propionic acid derivatives described in WO 2006/027680 to Hepworth et al. (Pfizer Inc.); JMV-390-1 (2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl)benzenepropionamide); RU-44004 (N-(4-morpholinyl)-3-phenyl-2-(sulfanylmethyl)propionamide); SCH-32615 ((S)—N—[N-(1-carboxy-2-phenylethyl)-L-phenylalanyl]-β-alanine) and its prodrug SCH-34826 ((S)-N-[N-[1-[[(2,2-dimethyl-1,3-dioxolan-4-yl)methoxy]carbonyl]-2-phenylethyl]-L-phenylalanyl]-(β-alanine); sialorphin; SCH-42495 (N-[2(S)-(acetylsulfanylmethyl)-3-(2-methylphenyl) propionyl]-L-methionine ethyl ester); spinorphin; SQ-28132 (N-[2-(mercaptomethyl)-1-oxo-3-phenylpropyl]leucine); SQ-28603 (N-[2-(mercaptomethyl)-1-oxo-3-phenylpropyl]-β-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl]-carbonyl]amino] cyclohexanecarboxylic acid); UK-447,841 (2-{1-[3-(4-chlorophenyl)propylcarbamoyl]-cyclopentylmethyl}-4-methoxybutyric acid); UK-505,749 ((R)-2-methyl-3-{1-[3-(2-methylbenzothiazol-6-yl)propylcarbamoyl]-cyclopentyl}propionic acid); 5-biphenyl-4-yl-4-(3-carboxypropionylamino)-2-methylpentanoic acid and 5-biphenyl-4-yl-4-(3-carboxypropionylamino)-2-methylpentanoic acid ethyl ester (WO 2007/056546); daglutril [(3S, 2'R)-3-{1-[2'-(ethoxycarbonyl)-4'-phenylbutyl]-cyclopentan-1-carbonylamino}-2,3,4,5-tetrahydro-2-oxo-1H-1-benzazepine-1-acetic acid] described in WO 2007/106708 to Khder et al. (Novartis AG); and combinations thereof. In a particular embodiment, the NEP inhibitor is selected from candoxatril, candoxatrilat, CGS-24128, phosphoramidon, SCH-32615, SCH-34826, SQ-28603, thiorphan, and combinations thereof. The NEP inhibitor will be administered in an amount sufficient to provide from about 20-800 mg per day, with typical daily dosages ranging from 50-700 mg per day, more commonly 100-600 or 100-300 mg per day.

In yet another embodiment, a crystalline form of the invention is administered in combination with a non-steroidal anti-inflammatory agent (NSAID). Representative NSAIDs include, but are not limited to: acemetacin, acetyl salicylic acid, alclofenac, alminoprofen, amfenac, amiprilose, amoxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lornoxicam, meclofenamate, meclofenamic acid, mefenamic acid, meloxicam, mesalamine, miroprofen, mofebutazone, nabumetone, naproxen, niflumic acid, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In yet another embodiment, a crystalline form of the invention is administered in combination with an anti-lipid agent. Representative anti-lipid agents include, but are not limited to, statins such as atorvastatin, fluvastatin, lovastatin, pravastatin, rosuvastatin and simvastatin; cholesteryl ester transfer proteins (CETPs); and combinations thereof.

In yet another embodiment, a crystalline form of the invention is administered in combination with an anti-diabetic agent. Representative anti-diabetic agents include, but are not limited to: injectable drugs such as insulin and insulin derivatives; orally effective drugs including biguanides such as metformin, glucagon antagonists, α-glucosidase inhibitors such as acarbose and miglitol, meglitinides such as repaglinide, oxadiazolidinediones, sulfonylureas such as chlorpropamide, glimepiride, glipizide, glyburide, and tolazamide, thiazolidinediones such as pioglitazone and rosiglitazone; and combinations thereof.

In one embodiment, a crystalline form of the invention is administered in combination with an anti-thrombotic agent. Representative anti-thrombotic agents include, but are not limited to, aspirin, anti-platelet agents, heparin, and combinations thereof. Compounds of the invention may also be administered in combination with a renin inhibitor, examples of which include, but are not limited to, aliskiren, enalkiren, remikiren, and combinations thereof. In another embodiment, a compound of the invention is administered in combination with an endothelin receptor antagonist, representative examples of which include, but are not limited to, bosentan, darusentan, tezosentan, and combinations thereof. Compounds of the invention may also be administered in combination with an endothelin converting enzyme inhibitor, examples of which include, but are not limited to, phosphoramidon, CGS 26303, and combinations thereof. In yet another embodiment, a crystalline form of the invention is administered in combination with an aldosterone antagonist, representative examples of which include, but are not limited to, eplerenone, spironolactone, and combinations thereof.

Combined therapeutic agents may also be helpful in further combination therapy with compounds of the invention. For example, a combination of the ACE inhibitor enalapril (in the maleate salt form) and the diuretic hydrochlorothiazide, which is sold under the mark Vaseretic®, or a combination of the calcium channel blocker amlodipine (in the besylate salt form) and the ARB olmesartan (in the medoxomil prodrug form), or a combination of a calcium channel blocker and a statin, all may also be used with the crystalline forms of the invention. Dual-acting agents may also be helpful in combination therapy with the crystalline forms of the invention. For example, angiotensin-converting enzyme/neprilysin (ACE/NEP) inhibitors such as: AVE-0848 ((4S,7S,12bR)-7-[3-methyl-2(S)-sulfanylbutyramido]-6-oxo-1,2,3,4,6,7,8,12b-octahydropyrido[2,1-a][2]benzazepine-4-carboxylic acid); AVE-7688 (ilepatril) and its parent compound; BMS-182657 (2-[2-oxo-3(S)-[3-phenyl-2(S)-sulfanylpropionamido]-2,3,4,5-tetrahydro-1H-1-benzazepin-1-yl]acetic acid); CGS-26303 ([N-[2-(biphenyl-4-yl)-1(S)-(1H-tetrazol-5-yl)ethyl]amino]methylphosphonic acid); CGS-35601 (N-[1-[4-methyl-2(S)-sulfanylpentanamido]cyclopentylcarbonyl]-L-tryptophan); fasidotril; fasidotrilate; enalaprilat; ER-32935 ((3R,6S,9aR)-6-[3(S)-methyl-2(S)-sulfanylpentanamido]-5-oxoperhydrothiazolo[3,2-a]azepine-3-carboxylic acid); gempatrilat; MDL-101264 ((4S,7S,12bR)-7-[2(S)-(2-morpholinoacetylthio)-3-phenylpropionamido]-6-oxo-1,2,3,4,6,7,8,12b-octahydropyrido[2,1-a][2]benzazepine-4-carboxylic acid); MDL-101287 ([4S-[4α,7αa(R*),12bβ-7-[2-(carboxymethyl)-3-phenylpropionamido]-6-oxo-1,2,3,4,6,7,8,12b-octahydropyrido[2,1-a][2]benzazepine-4-carboxylic acid); omapatrilat; RB-105 (N-[2(S)-(mercaptomethyl)-3(R)-phenylbutyl]-L-alanine); sampatrilat; SA-898 ((2R,4R)—N-[2-(2-hydroxyphenyl)-3-(3-mercaptopropionyl)thiazolidin-4-ylcarbonyl]-L-phenylalanine); Sch-50690 (N-[1(S)-carboxy-2-[N2-(methanesulfonyl)-L-lysylamino]ethyl]-L-valyl-L-tyrosine); and combinations thereof, may also be included. In one particular embodiment, the ACE/NEP inhibitor is selected from: AVE-7688, enalaprilat, fasidotril, fasidotrilate, omapatrilat, sampatrilat, and combinations thereof. Other therapeutic agents such as $\alpha_2$-adrenergic receptor agonists and vasopressin receptor antagonists may also be helpful in combination therapy. Exemplary $\alpha_2$-adrenergic receptor agonists include clonidine, dexmedetomidine, and guanfacine. Exemplary vasopressin receptor antagonists include tolvaptan.

The following formulations illustrate representative pharmaceutical compositions of the invention.

Exemplary Hard Gelatin Capsules for Oral Administration

A crystalline form of the invention (50 g), spray-dried lactose (440 g) and magnesium stearate (10 g) are thoroughly blended. The resulting composition is then loaded into hard gelatin capsules (500 mg of composition per capsule). Alternately, the crystalline form (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Exemplary Gelatin Capsule Formulation for Oral Administration

A crystalline form of the invention (100 mg) is thoroughly blended with polyoxyethylene sorbitan monooleate (50 mg) and starch powder (250 mg). The mixture is then loaded into a gelatin capsule (400 mg of composition per capsule).

Alternately, the crystalline form (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Tablet Formulation for Oral Administration

A crystalline form of the invention (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, the crystalline form (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, the crystalline form (400 mg) is thoroughly blended with cornstarch (50 mg), croscarmellose sodium (25 mg), lactose (120 mg), and magnesium stearate (5 mg). The mixture is then compressed to form a single-scored tablet (600 mg of composition per tablet).

Alternately, the crystalline form (100 mg) is thoroughly blended with cornstarch (100 mg) with an aqueous solution of gelatin (20 mg). The mixture is dried and ground to a fine powder. Microcrystalline cellulose (50 mg) and magnesium stearate (5 mg) are the admixed with the gelatin formulation, granulated and the resulting mixture compressed to form tablets (100 mg of active per tablet).

Exemplary Suspension Formulation for Oral Administration

The following ingredients are mixed to form a suspension containing 100 mg of active agent per 10 mL of suspension:

| Ingredients | Amount |
| --- | --- |
| Crystalline form | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Liquid Formulation for Oral Administration

A suitable liquid formulation is one with a carboxylic acid-based buffer such as citrate, lactate and maleate buffer solutions. For example, a crystalline form of the invention (which may be pre-mixed with DMSO) is blended with a 100 mM ammonium citrate buffer and the pH adjusted to pH 5, or with is blended with a 100 mM citric acid solution and the pH adjusted to pH 2. Such solutions may also include a solubilizing excipient such as a cyclodextrin, for example the solution may include 10 wt % hydroxypropyl-β-cyclodextrin.

Other suitable formulations include a 5% $NaHCO_3$ solution, with or without cyclodextrin.

Exemplary Injectable Formulation for Administration by Injection

A crystalline form of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions for Administration By Inhalation

A crystalline form of the invention (0.2 mg) is micronized and then blended with lactose (25 mg). This blended mixture is then loaded into a gelatin inhalation cartridge. The contents of the cartridge are administered using a dry powder inhaler, for example.

Alternately, a micronized crystalline form (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 10 μg to about 500 μg of the compound of the invention per dose when administered by the inhaler.

Alternately, the crystalline form (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1N sodium hydroxide. The solution is administered using a nebulizer device that provides about 10 μg to about 500 μg of the active agent per dose.

EXAMPLES

The following Preparations and Examples are provided to illustrate specific embodiments of this invention. These specific embodiments, however, are not intended to limit the scope of this invention in any way unless specifically indicated.

The following abbreviations have the following meanings unless otherwise indicated and any other abbreviations used herein and not defined have their standard generally accepted meaning:
EtOAc ethyl acetate
EtOH ethanol
MeCN acetonitrile
MeOH methanol
MTBE methyl t-butyl ether
THF tetrahydrofuran
TFA trifluoroacetic acid Unless noted otherwise, all materials, such as reagents, starting materials and solvents, were purchased from commercial suppliers (such as Sigma-Aldrich, Fluka Riedel-de Haën, Strem Chemicals, Inc., and the like) and were used without further purification.

Example 1

Preparation of Crystalline Hemiedisylate Salt Form I of 4'-{2-Ethoxy-4-ethyl-5-[((S)-2-mercapto-4-methylpentanoylamino)methyl]imidazol-1-ylmethyl}-3'-fluorobiphenyl-2-carboxylic Acid Vapor Diffusion Preparation Without Seeding 4'-{2-Ethoxy-4-ethyl-5-[((S)-2-mercapto-4-methylpentanoylamino)methyl]-imidazol-1-ylmethyl}-3'-fluorobiphenyl-2-carboxylic acid (840 mg) was dissolved in EtOH (33.6 mL) and an aliquot (0.6 mL, 1.0 eq.) was placed in a 4 mL vial. To this was added 1,2-ethanedisulfonic acid (63 μL of a 0.5M solution of 1,2-ethanedisulfonic acid in MeOH; 1.1. eq.). This 4 mL vial was placed in a 20 mL vial containing MTBE. The 20 mL vial was capped and stored at room temperature. Solids appeared, which were filtered, washed with dioxane, and dried to yield a solid material, which was used in the next step without further characterization.

4'-{2-Ethoxy-4-ethyl-5-[((S)-2-mercapto-4-methylpentanoylamino)methyl]-imidazol-1-ylmethyl}-3'-fluorobiphenyl-2-carboxylic acid (50 mg, 95 μmol, 1.0 eq.) was dissolved in warm EtOH (2 mL) in a 20 mL vial. A 0.5M solution of 1,2-ethanedisulfonic acid in MeOH (210 μL, 1.1 eq.) was added and the mixture was warmed briefly. This 20 mL vial was placed in a larger vial containing MTBE (10 mL). The 20 mL vial was then seeded with the solid material and the larger vial was then capped and stored at room temperature until solids were observed. The liquor was removed and the solids were washed with dioxane (1 mL) then dried under vacuum to yield a solid hemiedisylate material (~25 mg).

Hemiedisylate Seed Crystal Preparation

4'-{2-Ethoxy-4-ethyl-5-[((S)-2-mercapto-4-methylpentanoylamino)methyl]-imidazol-1-ylmethyl}-3'-fluorobiphenyl-2-carboxylic acid (0.2 g, 0.4 mmol, 1.0 eq.) was dissolved in EtOH (6.0 mL) with heat. 1,2-Ethanedisulfonic acid hydrate was dried at 60° C. under vacuum for 30 minutes to yield solid ethanedisulfonic acid. The solid ethanedisulfonic acid (79 mg, 420 μmol, 1.1. eq.) was added and the mixture was heated briefly to aid dissolution. MTBE (45 mL) was added until near saturation. The resulting mixture was seeded with the solid hemiedisylate material, and slowly stirred overnight. A fine precipitate appeared on the bottom of the vial, which was filtered, washed with dioxane, and dried to yield a solid white hemiedisylate material (70 mg)

Preparation With Seeding

4'-{2-Ethoxy-4-ethyl-5-[((S)-2-mercapto-4-methylpentanoylamino)methyl]-imidazol-1-ylmethyl}-3'-fluorobiphenyl-2-carboxylic acid (193 mg, 366 μmol, 1.0 eq.) was dissolved in EtOH (2 mL) with heat. 1,2-Ethanedisulfonic acid hydrate (83.8 mg, 402 μmol, 1.1. eq.) was added and the mixture was heated briefly to aid dissolution. MTBE (10 mL) was added until near saturation. The resulting mixture was filtered and the filtrate was seeded with the solid white hemiedisylate material. Solids appeared on the bottom of the vial, which were filtered, washed with dioxane, and dried under vacuum to yield a solid product (60 mg). This product was analyzed by powder X-ray diffraction, differential scanning calorimetry, and thermal gravimetric analysis, as described in the examples below, and was designated crystalline hemiedisylate salt form I. This data is presented in FIGS. 1-3.

Example 2

Preparation of Crystalline Hemiedisylate Salt Form II of 4'-{2-Ethoxy-4-ethyl-5-[((S)-2-mercapto-4-methylpentanoylamino)methyl]imidazol-1-ylmethyl}-3'-fluorobiphenyl-2-carboxylic Acid First Preparation With Seeding 4'-{2-Ethoxy-4-ethyl-5-[((S)-2-mercapto-4-methylpentanoylamino)methyl]-imidazol-1-ylmethyl}-3'-fluorobiphenyl-2-carboxylic acid (666 mg, 1.3 mmol, 1.0 eq.) was dissolved in EtOH (6.6 mL) with gentle heating. 1,2-Ethanedisulfonic acid hydrate was dried at 60° C. under vacuum for 30 minutes to yield solid ethanedisulfonic acid. The solid ethanedisulfonic acid (260 mg, 1.4 mmol, 1.1 eq.) was added to the mixture, which was heated briefly to aid dissolution. MTBE (25 mL) was added until near saturation. The resulting mixture was filtered and the filtrate was seeded with hemiedisylate salt form I. Solids appeared on the bottom of the flask, which were filtered, washed with dioxane, and dried under vacuum to yield a white solid (530 mg).

A portion of this white solid (430 mg) was dissolved in warm EtOH (1.7 mL). MTBE (6 mL) was added dropwise until near saturation point. The resulting mixture was filtered and then seeded with the white solid, and cooled at room temperature. The mixture was then filtered and the solids washed with dioxane. The solids were then dried overnight under vacuum to yield a white solid product (0.4 g). The white solid product crystals appeared larger and more well-formed than the crystals of the hemiedisylate salt form I starting material.

Subsequent Preparation With Seeding

4'-{2-Ethoxy-4-ethyl-5-[((S)-2-mercapto-4-methylpentanoylamino)methyl]-imidazol-1-ylmethyl}-3'-fluorobiphenyl-2-carboxylic acid (13.5 g, 25.6 mmol, 1.0 eq.) was mixed with 1,2-ethanedisulfonic acid (5.4 g, 28 mmol, 1.1. eq.). 10% Aqueous EtOH (0.9:0.1, EtOH:$H_2O$, 130 g, 2500 mmol) was added and the resulting mixture was stirred to aid dissolution (~5 minutes). The mixture was filtered, and EtOAc (1750 mL) was added to the filtrate in 250 mL portions until near saturation. The resulting mixture was seeded with hemiedisylate salt form I (10 mg), and allowed to sit at room temperature (covered). Solids appeared, which were filtered, washed with EtOH, and dried under vacuum to yield a white solid hemiedisylate product (13.9 g; purity 95%). This hemiedisylate product was analyzed by powder X-ray diffraction, differential scanning calorimetry, and thermal gravimetric analysis, as described in the examples below. It was determined that this hemiedisylate product was a different hemiedisylate crystalline form than the crystalline hemiedisylate salt form I seeding material, and was designated crystalline hemiedisylate salt form II. This data is presented in FIGS. 6-8.

Example 3

Preparation of Crystalline Hemiedisylate Salt Form II of 4'-{2-Ethoxy-4-ethyl-5-[((S)-2-mercapto-4-methylpentanoylamino)methyl]imidazol-1-ylmethyl}-3'-fluorobiphenyl-2-carboxylic Acid (Without Seeding)

1,2-Ethanedisulfonic acid hydrate was dried at 65° C. for 7 days under vacuum to yield solid ethanedisulfonic acid. The solid ethanedisulfonic acid (0.4 g, 2.1 mmol, 1.1 eq.) was combined with 4'-{2-ethoxy-4-ethyl-5-[((S)-2-mercapto-4-methylpentanoylamino)-methyl]imidazol-1-ylmethyl}-3'-fluorobiphenyl-2-carboxylic acid (1.0 g, 1.9 mmol, 1.0 eq.) and dissolved in 10% aqueous EtOH (0.9:0.1, EtOH:$H_2O$, 10 g, 200 mmol). EtOAc (150 mL) was added until near saturation. The resulting mixture was filtered and the solids were allowed to sit at room temperature for about 3 days, after which dense crystal growth was observed. The solids were filtered, washed with EtOH and dried under vacuum to yield 1.0 g of a solid. The product was then analyzed by powder X-ray diffraction, differential scanning calorimetry, and thermal gravimetric analysis. It was determined that this product was crystalline hemiedisylate salt form II.

Example 5

Reslurrying of Hemiedisylate Salt Form I and Hemiedisylate Salt Form II

Hemiedisylate salt form II (50 mg, 80 μmol) and hemiedisylate salt form I (50 mg, 80 μmol) were combined with a premixed solution of EtOH (420 μL) and MTBE (1.6 mL, 13 mmol). The mixture was capped and stirred at room temperature. The resulting solids were filtered and washed with dioxane to yield a solid (86 mg), which was determined to be hemiedisylate salt form II.

Hemiedisylate salt form II (50 mg, 80 μmol) and hemiedisylate salt form I (50 mg, 80 μmol) were combined with a premixed solution of EtOH (420 μL) and MTBE (1.6 mL, 13 mmol). Water (20 μL) was added and the mixture was capped and stirred at room temperature. The resulting solids were filtered and washed with dioxane to yield a solid (67 mg), which was determined to be hemiedisylate salt form II.

Therefore, crystalline hemiedisylate salt form II appears to be more stable than crystalline hemiedisylate salt form I. In addition, subsequent attempts to repeat the conditions described in Example 1, produced crystalline hemiedisylate salt form II instead of the crystalline hemiedisylate salt form I.

Example 6

Preparation of Crystalline Heminapadisylate Salt of 4'-{2-Ethoxy-4-ethyl-5-[((S)-2-mercapto-4-methylpentanoylamino)methyl]imidazol-1-ylmethyl}-3'-fluorobiphenyl-2-carboxylic Acid Preparation Without Seeding 4'-{2-Ethoxy-4-ethyl-5-[((S)-2-mercapto-4-methylpentanoylamino)methyl]-imidazol-1-ylmethyl}-3'-fluorobiphenyl-2-carboxylic acid (1.0 g, 1.9 mmol, 1.0 eq.) was mixed with napadisylate (0.6 g, 2.1 mmol, 1.1 eq.). EtOH (10 mL) was added, followed by sonication to facilitate dissolution, to yield a partly cloudy solution. Water (20 μL) was added, followed by the slow addition of EtOAc (50 mL) until near saturation. The mixture was filtered under vacuum, and the solids were allowed to sit at room temperature for about 3 days. The mixture was filtered, washed with EtOH and dried under vacuum to yield the title crystalline heminapadisylate (1.2 g).

Heminapadisylate Seed Crystal Preparation

Napadisylate (0.17 g, 0.58 mmol, 1.1. eq.) was dissolved in EtOH (3 mL). 4'-{2-Ethoxy-4-ethyl-5-[((S)-2-mercapto-4-methylpentanoylamino)methyl]-imidazol-1-ylmethyl}-3'-fluorobiphenyl-2-carboxylic acid (280 mg, 530 μmol, 1.0 eq.) was added and the mixture was briefly heated to aid dissolution. EtOAc (19 mL) was added until near saturation. The mixture was filtered and allowed to sit at room temperature, until a small amount of precipitate was observed. The solution was filtered, seeded with hemiedisylate salt form II, and allowed to stand at room temperature. The resulting crystals were filtered, washed with dioxane, and dried overnight under vacuum to yield a heminapadisylate solid (250 mg).

Napadisylate (960 mg, 3.3 mmol, 1.1. eq.) was dissolved in EtOH (20 mL). 4'-{2-Ethoxy-4-ethyl-5-[((S)-2-mercapto-4-methylpentanoylamino)methyl]-imidazol-1-ylmethyl}-3'-fluorobiphenyl-2-carboxylic acid (1.6 g, 3.0 mmol, 1.0 eq.) was added with stirring. EtOAc (180 mL) was slowly added, with stirring, until near saturation. The mixture was filtered, seeded with the heminapadisylate solid, and allowed to sit at room temperature overnight. The mixture was filtered, and the solids were washed with dioxane then dried for about 2 days under vacuum to yield the title crystalline heminapadisylate salt (1.4 g).

Subsequent Preparation With Seeding

4'-{2-Ethoxy-4-ethyl-5-[((S)-2-mercapto-4-methylpentanoylamino)methyl]-imidazol-1-ylmethyl}-3'-fluorobiphenyl-2-carboxylic acid (13.5 g, 25.6 mmol, 1.0 eq.) was mixed with napadisylate (8.1 g, 28 mmol, 1.1 eq.; previously ground in a mortar). EtOH (130 mL) was added with stirring, over 20 minutes, to yield a slightly hazy solution. The solution was filtered and EtOAc (640 mL) was added until near saturation, yielding a slightly hazy solution. The solution was filtered twice to yield a clear solution. The solution was then seeded with heminapadisylate (~10 mg), and allowed to stand at room temperature (covered). The resulting solids were filtered, washed with EtOH, and dried under vacuum to yield a white solid (16.9 g). A portion of this solid (510 mg) was mixed with EtOH (0.5 mL). Water was added (750 µL) in several aliquots to aid dissolution. EtOAc (15 mL) was added and the mixture was allowed to stand at room temperature until solids began to form. Additional EtOAc (15 mL) was added allowed to stand at room temperature. The resulting solids were filtered and washed with EtOH to yield the title crystalline heminapadisylate salt (0.1 g).

This product was then analyzed by powder X-ray diffraction, differential scanning calorimetry, and thermal gravimetric analysis, as described in the examples below, and was designated a crystalline heminapadisylate salt. This data is presented in FIGS. 11-13.

Example 7

Preparation of Crystalline Heminapadisylate Salt of 4'-{2-Ethoxy-4-ethyl-5-[((S)-2-mercapto-4-methyl-pentanoylamino)methyl]imidazol-1-ylmethyl}-3'-fluorobiphenyl-2-carboxylic Acid Napadisylate (3.7 g, 12.9 mmol, 0.55 eq.) was mixed with EtOH (100 mL) and sonicated to aid dissolution. The resulting solution was filtered and rinsed with EtOH (20 mL). 4'-{2-Ethoxy-4-ethyl-5[((S)-2-mercapto-4-methylpentanoylamino)methyl]-imidazol-1-ylmethyl}-3'-fluorobiphenyl-2-carboxylic acid (12.4 g, 23.5 mmol, 1.00 eq.) was added and the resulting mixture was stirred. EtOAc (1450 mL) was added until near saturation. The resulting mixture was filtered and then seeded with heminapadisylate, and allowed to stand at room temperature. The resulting solids were filtered, washed with EtOH, and dried overnight under vacuum to yield the title compound as a white crystalline solid (11.8 g).

Example 8

Preparation of Crystalline Mono-oxalate Salt of 4'-{2-Ethoxy-4-ethyl-5-[((S)-2-mercapto-4-methyl-pentanoylamino)methyl]imidazol-1-ylmethyl}-3'-fluorobiphenyl-2-carboxylic Acid Equimolar amounts of 4'-{2-ethoxy-4-ethyl-5-[((S)-2-mercapto-4-methylpentanoylamino)methyl]-imidazol-1-yl-methyl}-3'-fluorobiphenyl-2-carboxylic acid (2 g) and oxalic acid dihydrate (478 mg) were mixed and dissolved in a solution of MeCN (2 mL) and THF (2.5 mL) by stirring and sonication to yield a clear solution. EtOAc (40 mL) was added and the resulting solution was thoroughly mixed and allowed to evaporate under a mild nitrogen stream. A white solid formed after several hours of solvent evaporation, which was collected, filtered, and washed with excess EtOAc.

This product was then analyzed by powder X-ray diffraction, differential scanning calorimetry, and thermal gravimetric analysis, as described in the examples below, and was designated a crystalline mono-oxalate salt (purity >98%). This data is presented in FIGS. 17-19.

Example 9

Powder X-Ray Diffraction

Powder X-ray diffraction analysis of the solids was performed using the Rigaku MiniFlex X-ray diffractometer or the Thermo ARL X'Tra X-ray diffractometer. The X-ray source was Cu—Kα radiation (λ=1.54051 Å) with output voltage of 30 kV and current of 15 mA (Rigaku) or with output voltage of 45 kV and current of 40 mA (Thermo ARL). The instrument was operated in Bragg-Brentano geometry with incident, divergence, and scattering slits set to maximize the intensity at the sample. For measurement, a small amount of powder (5-25 mg) was gently pressed onto the sample holder to form a smooth surface and subjected to X-ray exposure. The samples were scanned in 2θ-2θ mode from 2° to 40° in 2θ with a step size of 0.03° and a scan speed of 2.0° per minute. The data acquisition was controlled by Rigaku Standard measurement software (Version 1.2.0.0) or Thermo ARL measurement software (Version 1.2.0.0) and analyzed by Jade software (Version 7.5.1). The instrument was calibrated with a silicon metal standard (Rigaku) or quartz standard (Thermo ARL), within ±0.02° two-theta angle.

It should be kept in mind that the Bragg-Brentano geometry used in the data collection is prone to preferred orientation. Under these conditions it is possible that the relative intensities of the diffraction peaks may not represent the true relative intensities that would be obtained from an idealized distribution of spherical particles or from a diffraction pattern simulated from a single crystal data. It is also possible that some peaks are not seen in some diffraction patterns due to the extensive preferred orientation.

Thermal Analysis

Differential scanning calorimetry (DSC) experiments were performed using a TA Instruments Model Q-100 module with a Thermal Analyst controller. Data were collected and analyzed using TA Instruments Universal Analysis software. A sample of each crystalline form was accurately weighed into a covered aluminum pan. After a 5 minute isothermal equilibration period at 5° C., the sample was heated using a linear heating ramp of 10° C./min from 0° C. to 200° C.

Thermogravimetric analysis (TGA) was performed using a TA Instruments Model Q-50 module equipped with high resolution capability. Data were collected using TA Instruments Thermal Analyst controller and analyzed using TA Instruments Universal Analysis software. A weighed sample was placed onto a platinum pan and scanned with a heating rate of 10° C. from ambient temperature to 200° C. The balance and furnace chambers were purged with nitrogen flow during use.

Dynamic Moisture Sorption Assessment

Dynamic moisture sorption (DMS) measurements were performed for each crystalline form using a VTI atmospheric microbalance, SGA-100 system (VTI Corp., Hialeah, Fla. 33016). A weighed sample was used and the humidity was set at the ambient value at the start of the analysis. The DMS analysis consisted of a scan rate of 5% RH/step over the full humidity range of 5% RH to 90% RH. The DMS run was performed isothermally at 25° C.

Thermal Stability

Weighed samples of the crystalline materials were stored at 40° C. (open container) and 75% relative humidity, for one month. The samples were then analyzed by the following HPLC method:

Column: Agilent Zorbox SB-C18, 4.6×250 mm, 5 μm (Part No. 880975-902). Mobile Phase A: 80% $H_2O$, 20% MeCN, 0.01% TFA. Mobile Phase B: 80% MeCN, 20% $H_2O$, 0.01% TFA. Flow rate: 1 mL/min. Injection Volume: 20 μL. Detector: 250 nm.

Samples were prepared as 0.2-0.5 mg/mL stock solutions in 100% MeCN, depending on the solubility, for injection onto the HPLC.

The purity of the samples was determined by HPLC area percentage (% AUC). As shown in the table below, all samples showed minimal loss of purity, thus showing that all forms had excellent thermal stability. However, the hemiedisylate form II and heminapadisylate form were found to be more stable than the previously known freebase form.

| Sample | Purity Change |
| --- | --- |
| freebase form* | −2.9% |
| hemiedisylate form II | −0.3% |
| heminapadisylate form | −0.1% |

*Prepared as described in U.S. Patent Publication No. 2010/0081697 to Chao et al.

Solubility

Samples of the crystalline materials were evaluated over a 24 hour period at several pH ranges. The following buffer systems were used:
HCl buffer pH @ 1.15
HCl buffer pH @ 1.94
Potassium biphthate buffer pH @ 2.97
Acetate buffer pH @ 4.17
Acetate buffer pH @ 5.16
Phosphate buffer pH @ 6.04
Phosphate buffer pH @ 7.0

Samples (7-8 mg) of the crystalline materials were combined with 2 mL of each of the buffers in a 5 mL glass vial. The vials were then mounted onto an automatic rotator and rotate for 24 hours at room temperature. The resulting suspensions were filtered using a 0.45 μm filter (PVDF membrane) into a clean vial for HPLC analysis.

Figure 16:
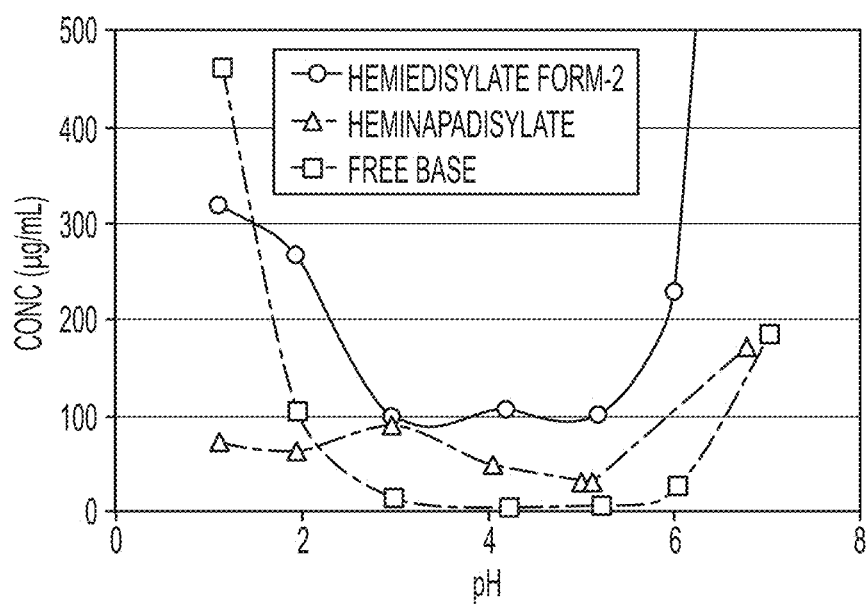
FIG. 16 shows the solubility profile of the crystalline hemiedisylate salt form II, the crystalline heminapadisylate salt, and the previously described crystalline freebase form.

Both the hemiedisylate form II and the heminapadisylate form were found to be more soluble than the freebase at pH>3, as detailed in FIG. 16.

X-Ray Structure Analysis

A chunk crystal of crystalline heminapadisylate having dimensions of 0.45×0.40×0.15 mm was mounted on a glass fiber. X-ray structure data was obtained using a Nonius Kappa CCD diffractometer using Mo Kα radiation. Data was collected at a temperature of 120±2° K. and was analyzed using SHELXS-97 and SHELXL-97 software. The following lattice parameters were derived: unit cell is triclinic with dimensions a=9.199(1) Å, b=10.556(1) Å, c=19.348(3) Å; α=80.754(8)°, β=79.286(7)°, γ=66.111(6)°, space group is P1bar; calculated density is 1.337 g/cm$^3$. Powder x-ray diffraction peaks calculated from the derived atomic positions were in excellent agreement with the observed results obtained using bulk powder sample.

The resulting molecular structure confirms the chemical composition is that of the compound of formula I and that the asymmetric unit contains two symmetry independent {2-ethoxy-4-ethyl-5-[((S)-2-mercapto-4-methylpentanoylamino)methyl]imidazol-1-ylmethyl}-3'-fluorobiphenyl-2-carboxylic acid molecules, one naphthalenedisulfonate anion, and water leading to the determination that this crystal is a hydrate. In this particular experiment, approximately half molecule of water was observed.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A solid pharmaceutical composition comprising a blended mixture of a pharmaceutically acceptable carrier and a crystalline heminapadisylate salt of 4'-{2-ethoxy-4-ethyl-5-[((S)-2-mercapto-4-methylpentanoylamino)methyl]imidazol-1-ylmethyl}-3'-fluorobiphenyl-2-carboxylic acid, characterized by a powder x-ray diffraction pattern comprising diffraction peaks at 2θ values of 4.84±0.20, 9.41±0.20, 10.82±0.20, 17.39±0.20, 24.17±0.20, and 24.65±0.20; wherein said composition is shaped or loaded into tablets or capsules.

2. The pharmaceutical composition of claim 1, wherein the crystalline heminapadisylate salt is further characterized by having one or more additional diffraction peaks at 2θ values selected from 14.05±0.20, 18.65±0.20, 19.55±0.20, 20.21±0.20, 21.44±0.20, 23.48±0.20, 25.69±0.20, 26.65±0.20, 28.79±0.20, 29.63±0.20, and 30.52±0.20.

3. The pharmaceutical composition of claim 1, wherein the crystalline heminapadisylate salt is characterized by a powder x-ray diffraction pattern in which the peak positions are substantially in accordance with the peak positions of the pattern shown in FIG. 11.

4. The pharmaceutical composition of claim 1, wherein the crystalline heminapadisylate salt is characterized by a differential scanning calorimetry thermogram which has a melting point of about 181° C.

5. The pharmaceutical composition of claim 1, wherein the crystalline heminapadisylate salt is characterized by a differential scanning calorimetry thermogram substantially in accordance with that shown in FIG. 12.

6. The pharmaceutical composition of claim 1, further comprising a secondary therapeutic agent selected from diuretics, $\beta_1$ adrenergic receptor blockers, calcium channel blockers, angiotensin-converting enzyme inhibitors, $AT_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, and combinations thereof.

7. A method for treating hypertension or heart failure, comprising administering the pharmaceutical composition of claim 1 to a patient in need of treatment.

* * * * *